US011413040B2

(12) United States Patent
Zeiner et al.

(10) Patent No.: US 11,413,040 B2
(45) Date of Patent: Aug. 16, 2022

(54) APPARATUS AND METHOD TO APPLY BUTTRESS TO END EFFECTOR OF SURGICAL STAPLER WITH AUTHENTICATION

(71) Applicant: Ethicon LLC, Guaynabo, PR (US)

(72) Inventors: Mark S. Zeiner, Mason, OH (US); Heather Strang, West Chester, OH (US); Pamela M. Ridgley, Lebanon, OH (US); Christopher A. Denzinger, Cincinnati, OH (US); Christopher Q. Seow, Cincinnati, OH (US); Michael J. Vendely, Lebanon, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/022,442

(22) Filed: Sep. 16, 2020

(65) Prior Publication Data

US 2022/0079584 A1    Mar. 17, 2022

(51) Int. Cl.
*A61B 17/072* (2006.01)
*A61B 17/068* (2006.01)
(Continued)

(52) U.S. Cl.
CPC ........ *A61B 17/0686* (2013.01); *A61B 17/072* (2013.01); *A61B 17/07207* (2013.01);
(Continued)

(58) Field of Classification Search
CPC . A61B 17/068; A61B 17/0686; A61B 17/072; A61B 17/07207; A61B 17/115;
(Continued)

(56) References Cited

U.S. PATENT DOCUMENTS 4,930,674 A    6/1990  Barak
5,358,510 A   10/1994  Luscombe et al.
(Continued)

FOREIGN PATENT DOCUMENTS

EP    2 090 248 A2    8/2009
EP    3 072 460 A2    9/2016
(Continued)

OTHER PUBLICATIONS

U.S. Appl. No. 17/022,186, entitled "Apparatus and Method to Apply Buttress to End Effector of Surgical Stapler via Fixed Base," filed Sep. 16, 2020.
(Continued)

*Primary Examiner* — Scott A Smith
(74) *Attorney, Agent, or Firm* — Frost Brown Todd LLC

(57) ABSTRACT

An apparatus includes a platform, an adjunct material, and an engagement feature. The platform includes an upper support and a lower support. The adjunct material is positioned on the upper support or the lower support. The upper support is configured to move relative to the lower support to apply the adjunct material to a jaw of an end effector incorporated into a surgical stapler. The engagement feature is configured to interact with a predetermined portion of the end effector to permit movement of the upper support relative to the lower support and thereby apply the adjunct material to the jaw of the end effector. The engagement feature is further configured to inhibit movement of the upper support relative to the lower support when the engagement feature is disengaged from the predetermined portion of the end effector.

20 Claims, 25 Drawing Sheets

(51) Int. Cl.
*A61B 17/28* (2006.01)
*A61B 17/00* (2006.01)

(52) U.S. Cl.
CPC ...... *A61B 17/07292* (2013.01); *A61B 17/282* (2013.01); *A61B 17/068* (2013.01); *A61B 2017/00398* (2013.01); *A61B 2017/07214* (2013.01); *A61B 2017/07257* (2013.01); *A61B 2017/07271* (2013.01); *A61B 2017/2825* (2013.01)

(58) Field of Classification Search
CPC ............ A61B 17/282; A61B 17/07292; A61B 2017/07214; A61B 2017/07271; A61B 2017/07257; A61B 2017/00398; A61B 2017/2825
USPC ..... 227/19, 175.2, 176.1, 180.1; 606/1, 139, 606/153, 219
See application file for complete search history.

(56) References Cited

U.S. PATENT DOCUMENTS

| | | | |
|---|---|---|---|
| 5,372,868 A | 12/1994 | Prewo et al. | |
| 5,655,698 A | 8/1997 | Yoon | |
| 5,697,542 A | 12/1997 | Knodel et al. | |
| 5,752,965 A * | 5/1998 | Francis | A61B 17/07207 227/178.1 |
| 5,769,892 A * | 6/1998 | Kingwell | A61B 17/07207 227/178.1 |
| 5,810,855 A * | 9/1998 | Rayburn | A61B 17/07207 227/176.1 |
| 5,833,695 A | 11/1998 | Yoon | |
| 5,901,895 A | 5/1999 | Heaton et al. | |
| 5,902,312 A | 5/1999 | Frater et al. | |
| 6,019,791 A * | 2/2000 | Wood | A61F 2/2445 623/2.11 |
| 6,099,551 A * | 8/2000 | Gabbay | A61B 17/07207 227/176.1 |
| 6,273,897 B1 * | 8/2001 | Dalessandro | A61B 17/07207 606/139 |
| 6,325,810 B1 | 12/2001 | Hamilton et al. | |
| 6,592,597 B2 * | 7/2003 | Grant | A61B 17/072 606/151 |
| 6,638,285 B2 * | 10/2003 | Gabbay | A61B 17/072 606/139 |
| 7,147,138 B2 * | 12/2006 | Shelton, IV | A61B 17/07207 227/176.1 |
| 7,377,928 B2 * | 5/2008 | Zubik | A61B 17/072 606/151 |
| 7,380,696 B2 | 6/2008 | Shelton, IV et al. | |
| 7,559,937 B2 | 7/2009 | De La Torre et al. | |
| 7,665,646 B2 | 2/2010 | Prommersberger | |
| 7,708,180 B2 * | 5/2010 | Murray | A61B 17/07292 227/175.1 |
| 7,845,533 B2 * | 12/2010 | Marczyk | A61B 17/07207 227/175.1 |
| 8,052,697 B2 | 11/2011 | Phillips | |
| 8,210,411 B2 | 7/2012 | Yates et al. | |
| 8,348,130 B2 | 1/2013 | Shah et al. | |
| 8,408,439 B2 | 4/2013 | Huang et al. | |
| 8,453,914 B2 | 6/2013 | Laurent et al. | |
| 8,464,925 B2 | 6/2013 | Hull et al. | |
| 8,864,009 B2 | 10/2014 | Shelton, IV et al. | |
| 9,186,142 B2 | 11/2015 | Fanelli et al. | |
| 9,220,501 B2 | 12/2015 | Baxter, III et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,999,408 B2 | 6/2018 | Boudreaux et al. | |
| 10,092,292 B2 | 10/2018 | Boudreaux et al. | |
| 10,166,023 B2 | 1/2019 | Vendely et al. | |
| 10,213,198 B2 | 2/2019 | Aronhalt et al. | |
| 10,349,939 B2 | 7/2019 | Shelton, IV et al. | |
| 10,932,779 B2 | 3/2021 | Vendely et al. | |
| 10,993,716 B2 | 5/2021 | Shelton, IV et al. | |
| 11,033,269 B2 | 6/2021 | Vendely et al. | |
| 11,045,196 B2 | 6/2021 | Olson et al. | |
| 11,051,812 B2 | 7/2021 | Hopkins et al. | |
| 11,058,418 B2 | 7/2021 | Shelton, IV et al. | |
| 2005/0267325 A1 | 12/2005 | Bouchier et al. | |
| 2006/0173470 A1 | 8/2006 | Oray et al. | |
| 2007/0162056 A1 | 7/2007 | Gerbi et al. | |
| 2007/0179528 A1 | 8/2007 | Soltz et al. | |
| 2007/0246505 A1 | 10/2007 | Pace-Floridia et al. | |
| 2008/0128469 A1 | 6/2008 | Dalessandro et al. | |
| 2008/0169329 A1 | 7/2008 | Shelton et al. | |
| 2008/0203134 A1 | 8/2008 | Shah et al. | |
| 2009/0001122 A1 | 1/2009 | Prommersberger et al. | |
| 2009/0084825 A1 | 4/2009 | Larson | |
| 2009/0206126 A1 | 8/2009 | Huitema et al. | |
| 2010/0087840 A1 | 4/2010 | Ebersole et al. | |
| 2010/0163598 A1 | 7/2010 | Belzer | |
| 2011/0017802 A1 | 1/2011 | Ma et al. | |
| 2011/0087279 A1 | 4/2011 | Shah et al. | |
| 2011/0248064 A1 | 10/2011 | Marczyk | |
| 2012/0018487 A1 | 1/2012 | Bettuchi et al. | |
| 2012/0080336 A1 | 4/2012 | Shelton, IV et al. | |
| 2012/0265154 A1 | 10/2012 | Criscuolo et al. | |
| 2013/0037596 A1 | 2/2013 | Bear et al. | |
| 2013/0075447 A1 | 3/2013 | Weisenburgh, II | |
| 2013/0146642 A1 | 6/2013 | Shelton, IV et al. | |
| 2013/0256378 A1 | 10/2013 | Schmid et al. | |
| 2014/0058194 A1 | 2/2014 | Soletti et al. | |
| 2014/0131418 A1 | 5/2014 | Kostrzewski | |
| 2014/0131419 A1 | 5/2014 | Bettuchi | |
| 2014/0158741 A1 | 6/2014 | Woodard, Jr. et al. | |
| 2014/0239036 A1 | 8/2014 | Zerkle et al. | |
| 2014/0288386 A1 | 9/2014 | Zand et al. | |
| 2014/0291379 A1 | 10/2014 | Schellin et al. | |
| 2015/0041168 A1 | 2/2015 | Dostinov | |
| 2015/0076212 A1 | 3/2015 | Shelton, IV | |
| 2015/0351761 A1 | 12/2015 | Shelton, IV et al. | |
| 2017/0055980 A1 | 3/2017 | Vendely et al. | |
| 2017/0056016 A1 | 3/2017 | Barton et al. | |
| 2017/0056018 A1 | 3/2017 | Zeiner et al. | |
| 2017/0281181 A1 | 10/2017 | Matonick et al. | |
| 2017/0303952 A1 | 10/2017 | Nativ et al. | |
| 2018/0235617 A1 | 8/2018 | Shelton, IV et al. | |
| 2018/0235626 A1 | 8/2018 | Shelton, IV et al. | |
| 2019/0290267 A1 | 9/2019 | Baxter, III et al. | |
| 2019/0321044 A1 | 10/2019 | Franklin, Sr. | |
| 2020/0015817 A1 | 1/2020 | Harris et al. | |
| 2020/0205823 A1 | 7/2020 | Vendely et al. | |
| 2020/0205825 A1 | 7/2020 | Vendely et al. | |
| 2020/0261080 A1 | 8/2020 | Bakos et al. | |
| 2020/0281587 A1 | 9/2020 | Schmid et al. | |
| 2020/0405436 A1 | 12/2020 | Shelton, IV et al. | |

FOREIGN PATENT DOCUMENTS

| | | |
|---|---|---|
| EP | 3 632 342 A2 | 4/2020 |
| EP | 3 673 831 A2 | 7/2020 |

OTHER PUBLICATIONS

U.S. Appl. No. 17/022,209, entitled "Apparatus and Method to Apply Buttress to End Effector of Surgical Stapler via Driven Member," filed Sep. 16, 2020.

U.S. Appl. No. 17/022,214, entitled "Apparatus and Method to Apply Buttresses Separately to Jaws of End Effector of Surgical Stapler," filed Sep. 16, 2020.

U.S. Appl. No. 17/022,414, entitled "Apparatus and Method to Close End Effector of Surgical Stapler onto Buttress," filed Sep. 16, 2020.

U.S. Appl. No. 17/022,419, entitled "Apparatus and Method to Detect Full Seating of Buttress Applicator in End Effector of Surgical Stapler," filed Sep. 16, 2020.

(56) References Cited

OTHER PUBLICATIONS

U.S. Appl. No. 17/022,520, entitled "Method of Applying Buttress to End Effector of Surgical Stapler," filed Sep. 16, 2020.
U.S. Appl. No. 17/022,186.
U.S. Appl. No. 17/022,209.
U.S. Appl. No. 17/022,214.
U.S. Appl. No. 17/022,414.
U.S. Appl. No. 17/022,419.
U.S. Appl. No. 17/022,520.
Gore Seamguard Bioabsorbable Staple Line Reinforcement, Configured for Endoscopic Surgical Staplers, Instructions for Use, Jun. 2019, 136 pgs.
International Search Report and Written Opinion dated Nov. 30, 2021 for Application No. PCT/IB2021/058337, 16 pgs.
International Search Report and Written Opinion dated Nov. 29, 2021 for Application No. PCT/IB2021/058165, 14 pgs.
International Search Report and Written Opinion dated Dec. 2, 2021 for Application No. PCT/IB2021/058414, 14 pgs.
International Search Report and Written Opinion dated Feb. 16, 2022 for Application No. PCT/IB2021/060163, 15 pgs.
International Search Report and Written Opinion dated Nov. 30, 2021 for Application No. PCT/IB2021/058396, 14 pgs.
International Search Report and Written Opinion dated Dec. 2, 2021 for Application No. PCT/IB2021/058412, 15 pgs.
International Search Report and Written Opinion dated Nov. 25, 2021 for Application No. PCT/IB2021/058400, 15 pgs.

\* cited by examiner

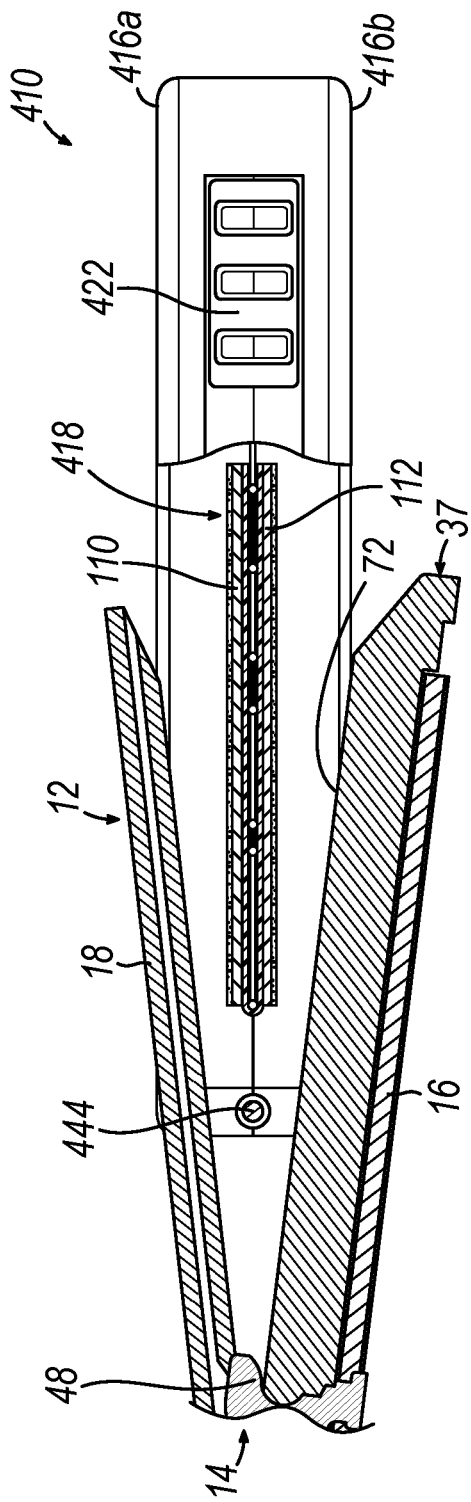
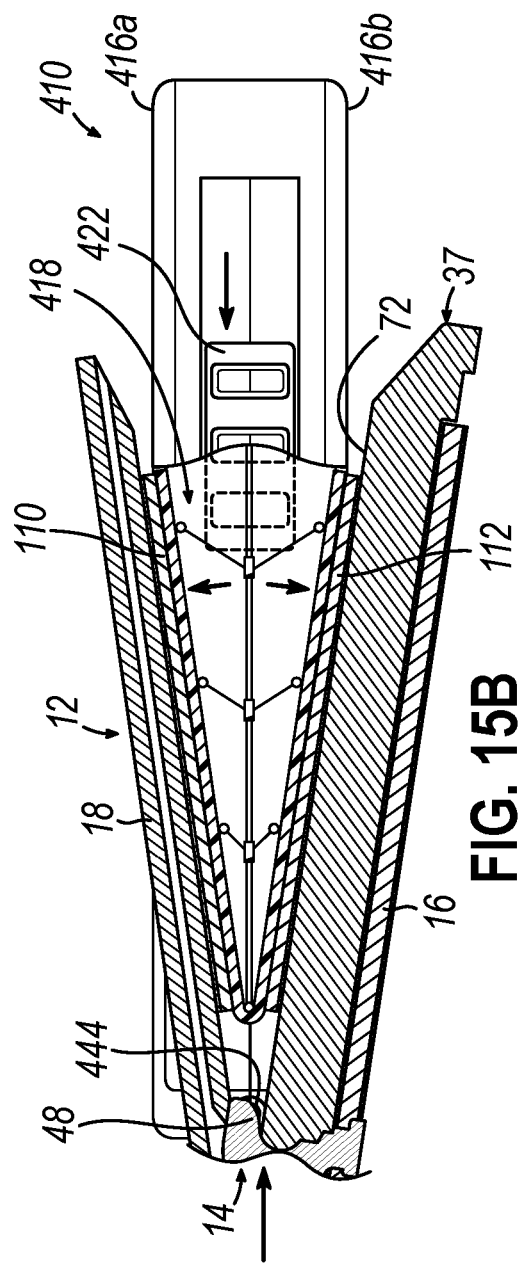
FIG. 15A
FIG. 15B

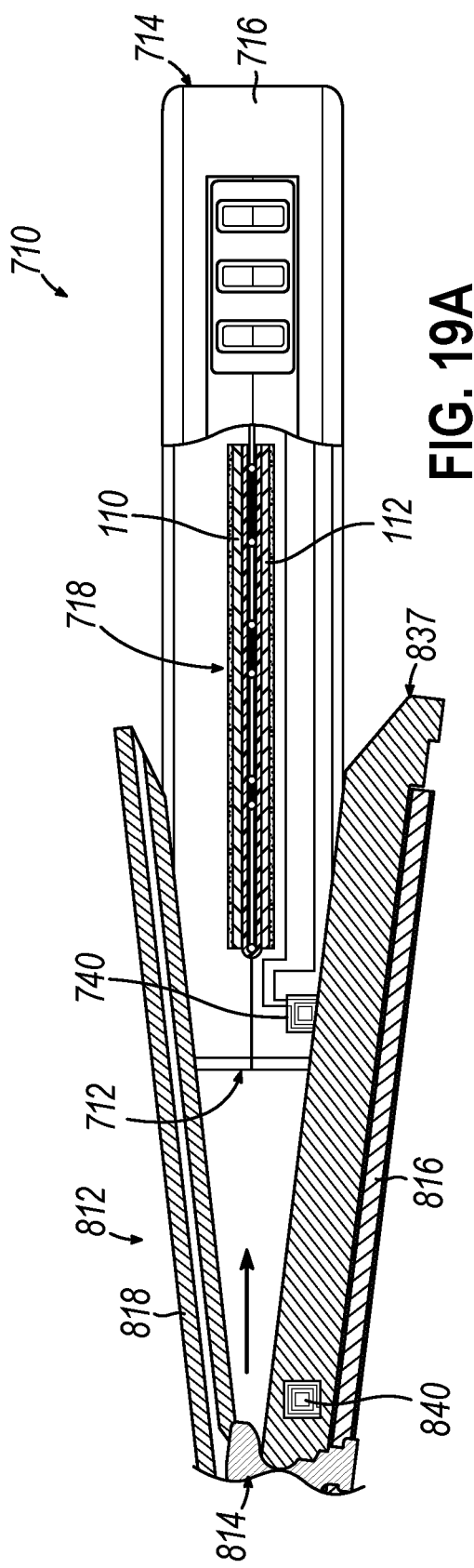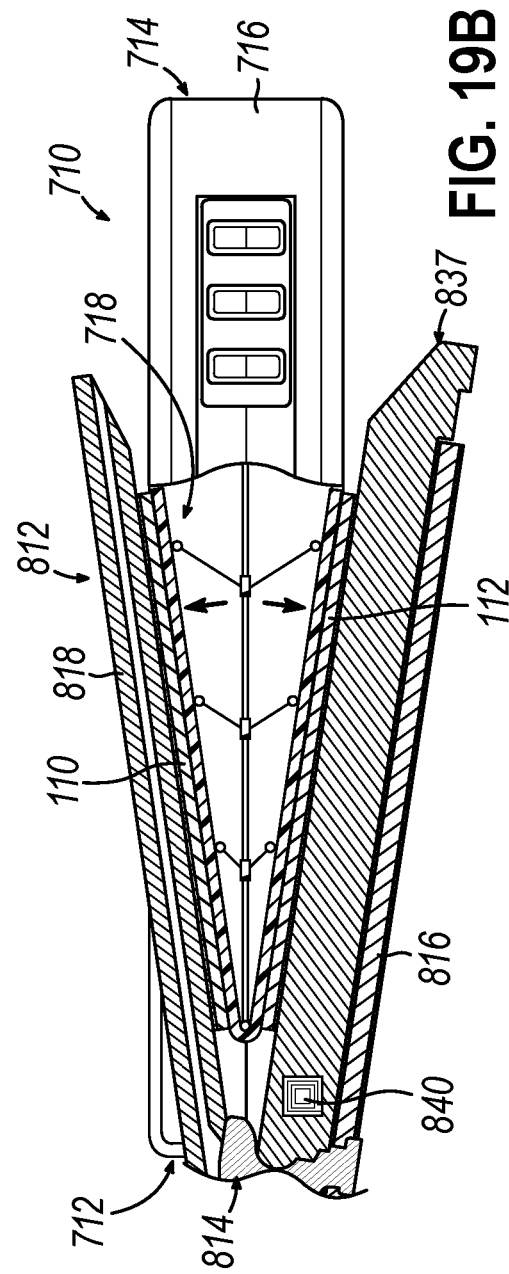

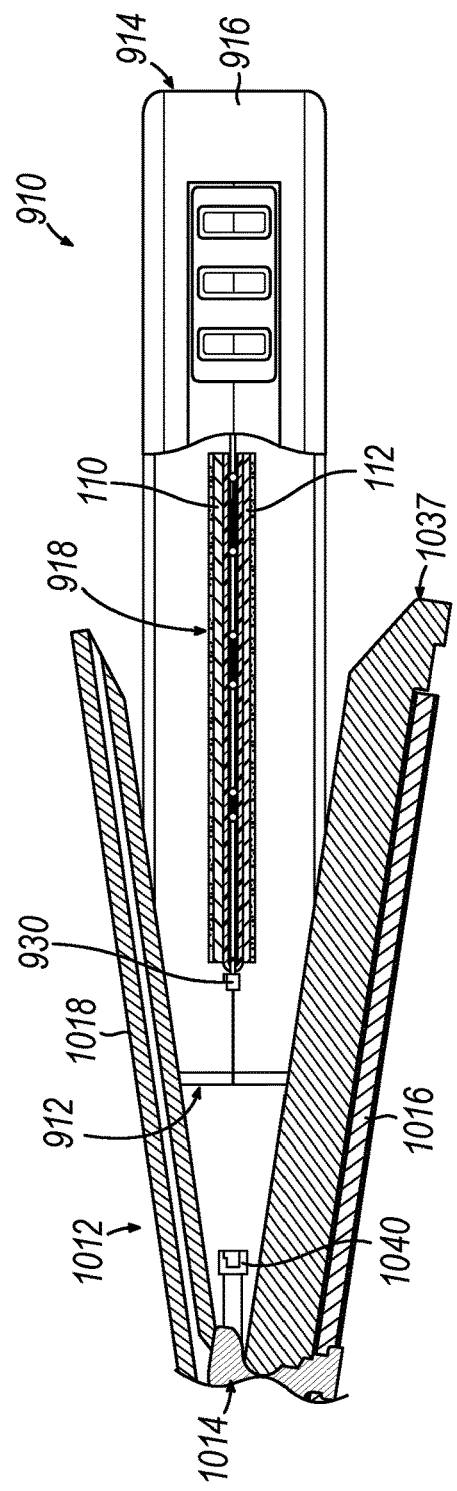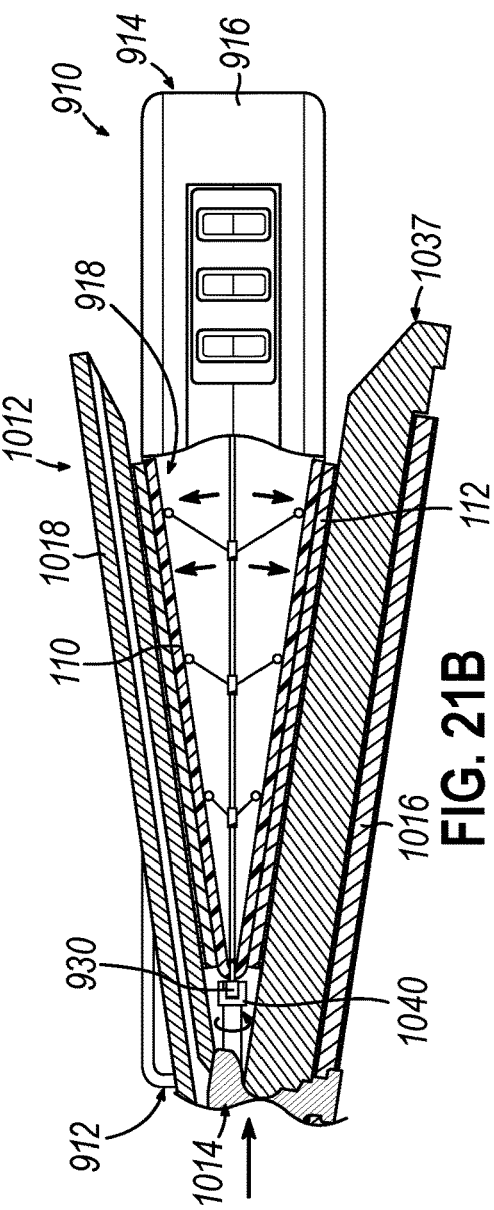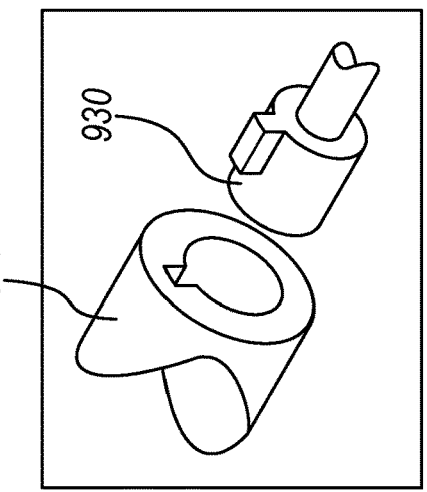
FIG. 21A
FIG. 21B
FIG. 22

APPARATUS AND METHOD TO APPLY BUTTRESS TO END EFFECTOR OF SURGICAL STAPLER WITH AUTHENTICATION

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 15A depicts a side partial cross-sectional view of the buttress applier cartridge of FIG. 14A, with the end effector of FIG. 3 being inserted into the buttress applier cartridge;

FIG. 15B depicts another side partial cross-sectional view of the buttress applier cartridge of FIG. 14A, with the end effector of FIG. 3 fully inserted into the buttress applier cartridge and a platform of the buttress applier cartridge in an expanded configuration;

FIG. 19A depicts a side partial cross-sectional view of still another buttress applier cartridge that may be used to carry and apply the buttress assemblies of FIG. 8, showing an end effector being inserted into the buttress applier cartridge;

FIG. 19B depicts another side partial cross-sectional view of the buttress applier cartridge of FIG. 19A, showing the end effector of FIG. 19A being fully inserted into the buttress applier cartridge;

FIG. 21A depicts a side partial cross-sectional view of still another buttress applier cartridge that may be used to carry and apply the buttress assemblies of FIG. 8, showing an end effector being inserted into the buttress applier cartridge;

FIG. 21B depicts another side partial cross-sectional view of the buttress applier cartridge of FIG. 21A, showing the end effector of FIG. 21A being fully inserted into the buttress applier cartridge;

FIG. 22 depicts a detailed perspective view of a power input and a power output of the buttress applier cartridge of FIG. 21A and the end effector of FIG. 21A, respectively;

Figure 1:
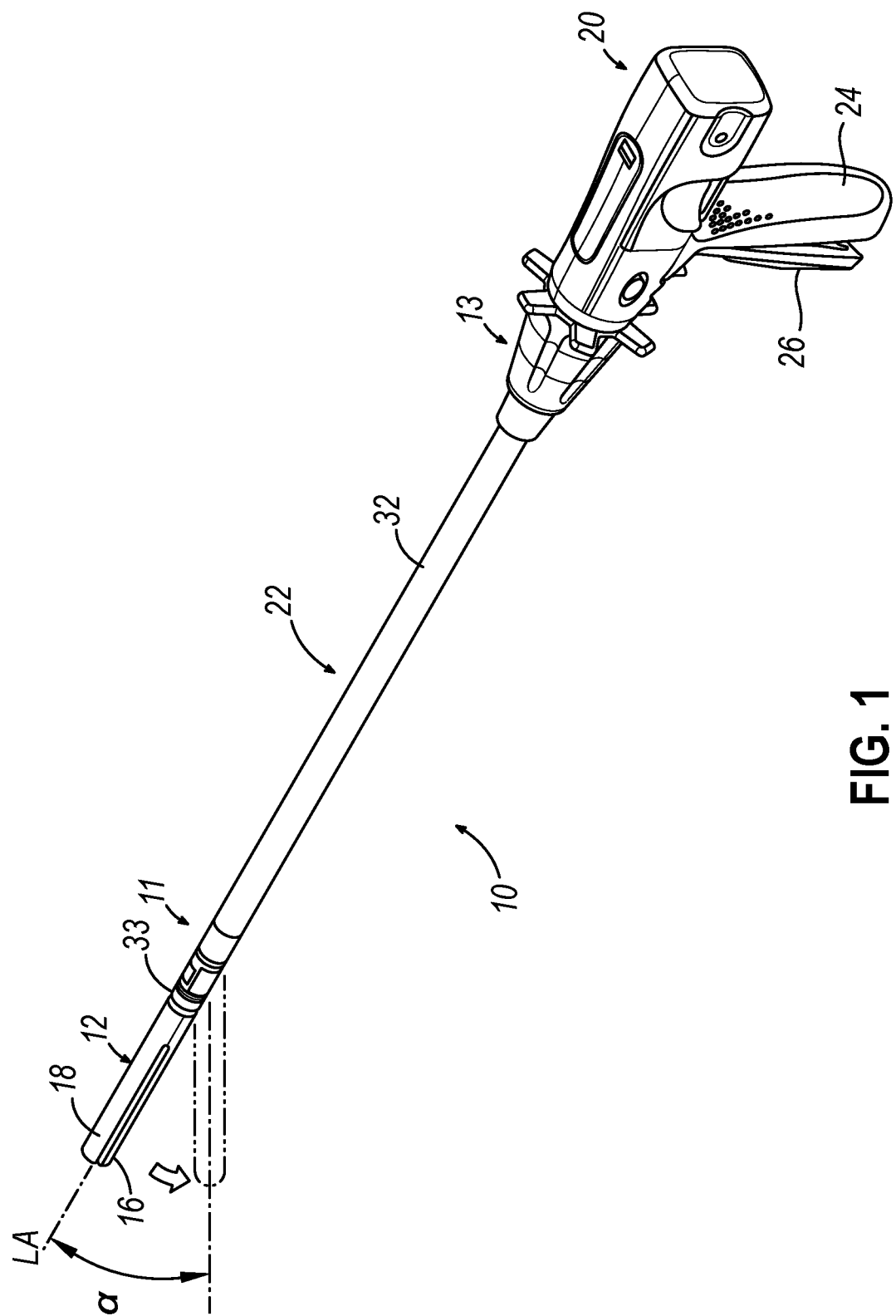
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
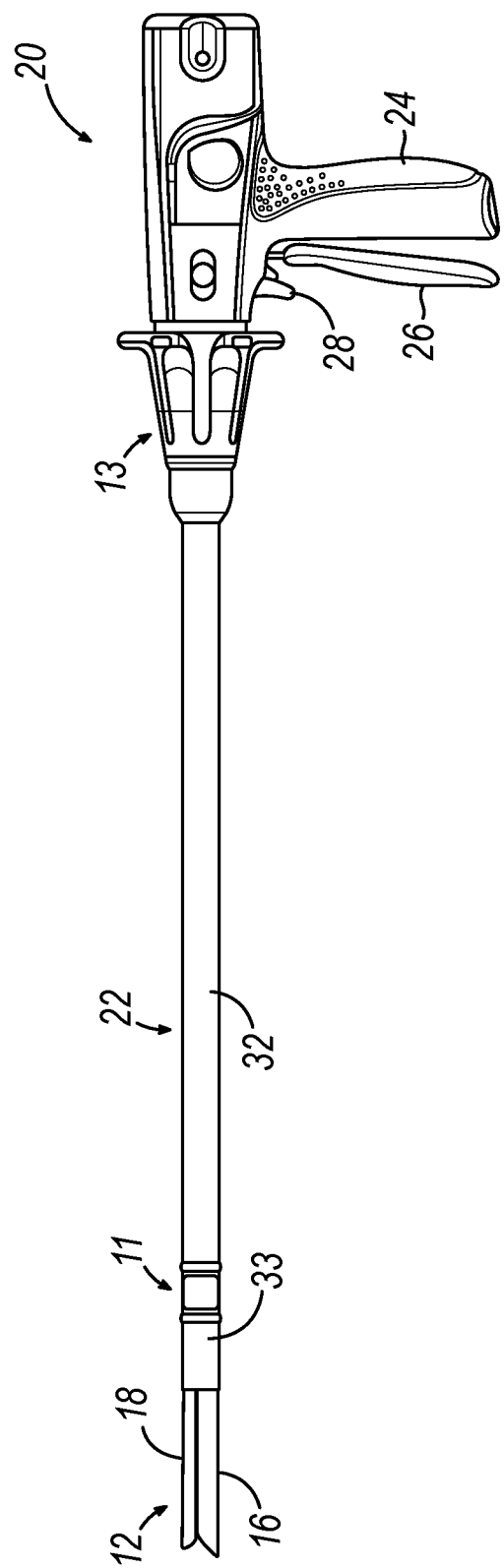
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
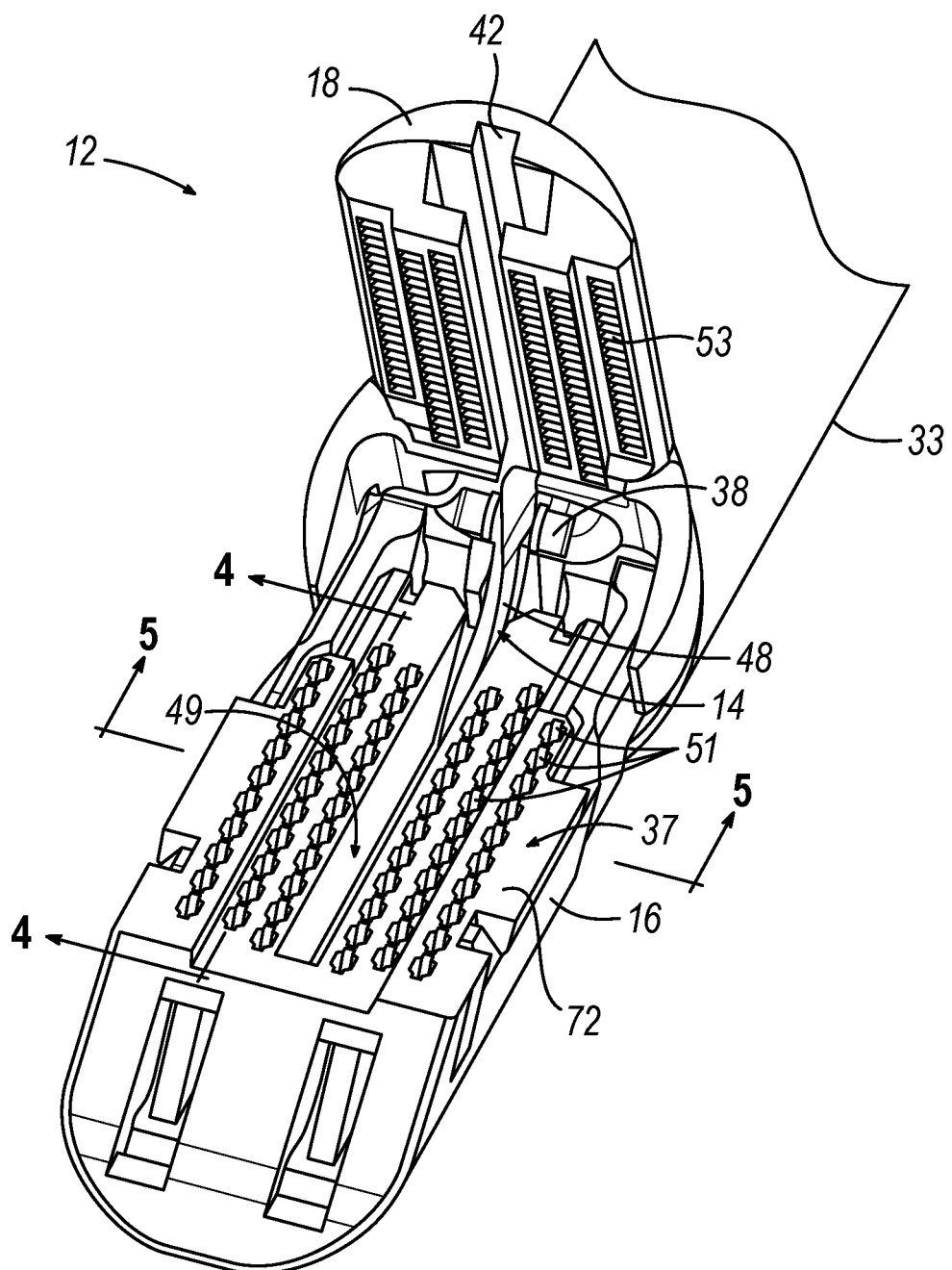
FIG. 3 depicts a perspective view of an end effector of the instrument of FIG. 1 in an open state.
Figure 4A:
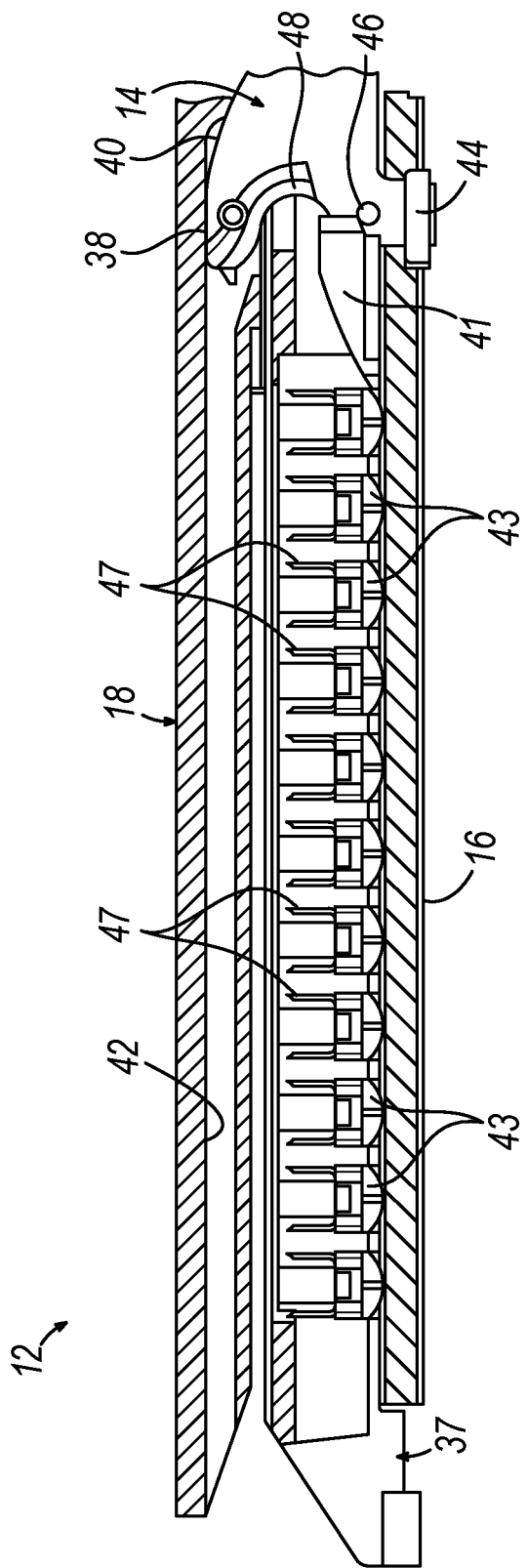
FIG. 4A depicts a side cross-sectional view of the end effector of FIG. 3, taken along line 4-4 of FIG. 3, with a firing beam in a proximal position.
Figure 4B:
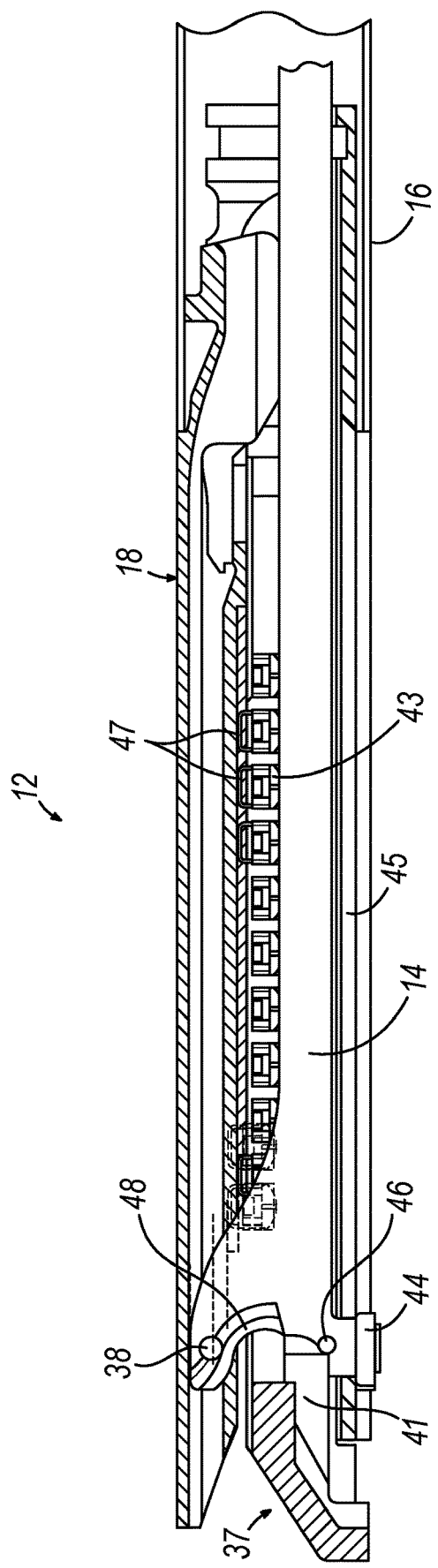
FIG. 4B depicts a side cross-sectional view of the end effector of FIG. 3, taken along line 4-4 of FIG. 3, with the firing beam in a distal position.
Figure 5:
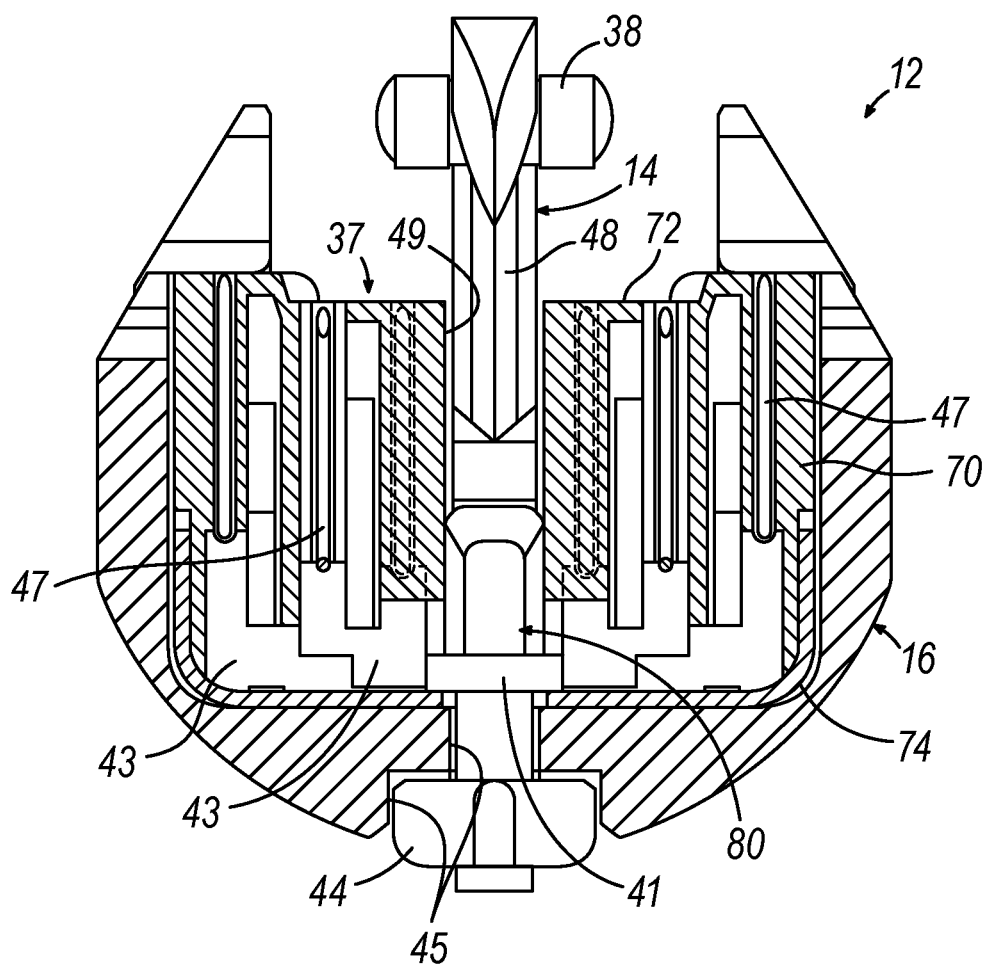
FIG. 5 depicts an end cross-sectional view of the end effector of FIG. 3, taken along line 5-5 of FIG. 3.
Figure 6:
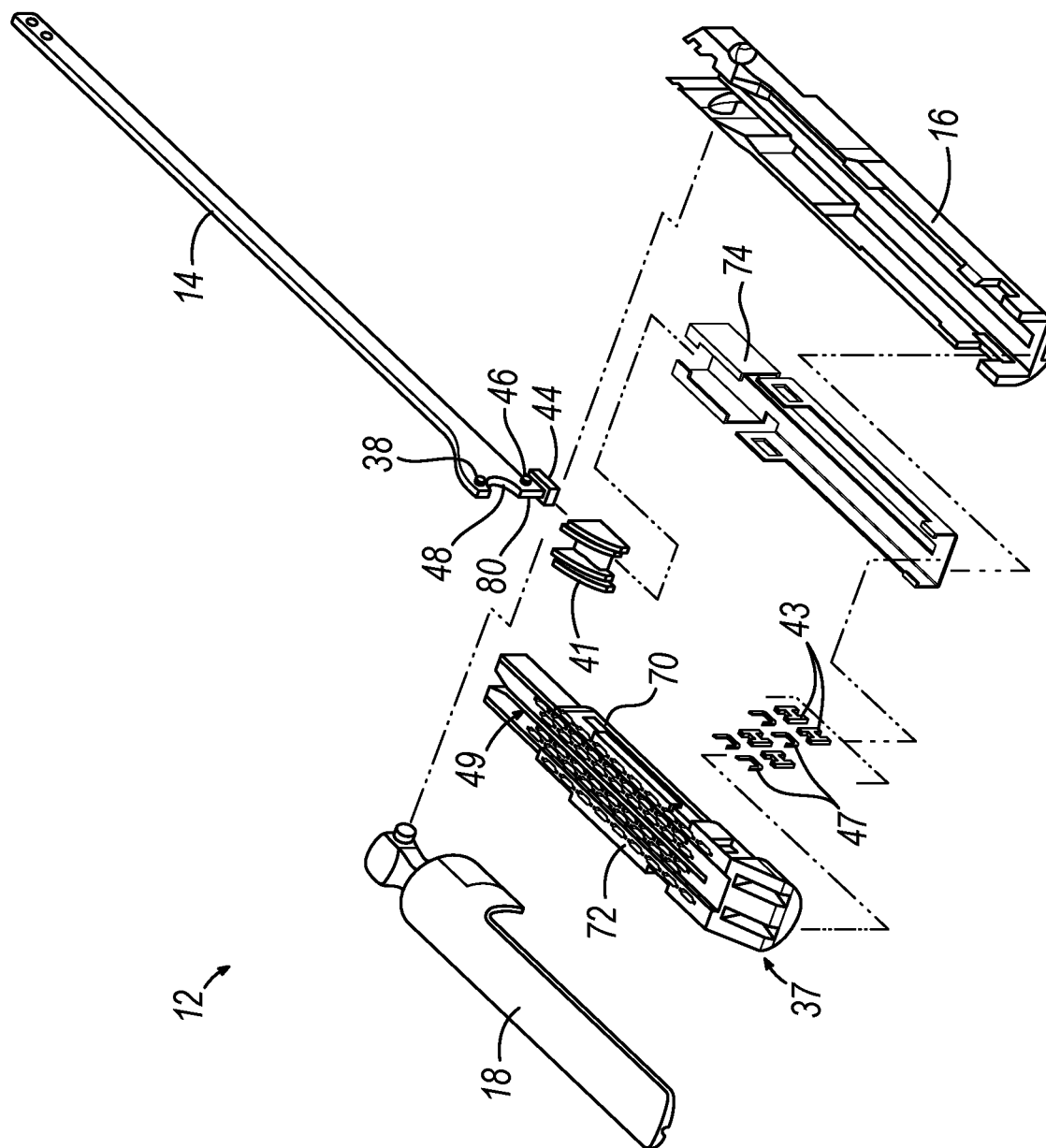
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at the distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
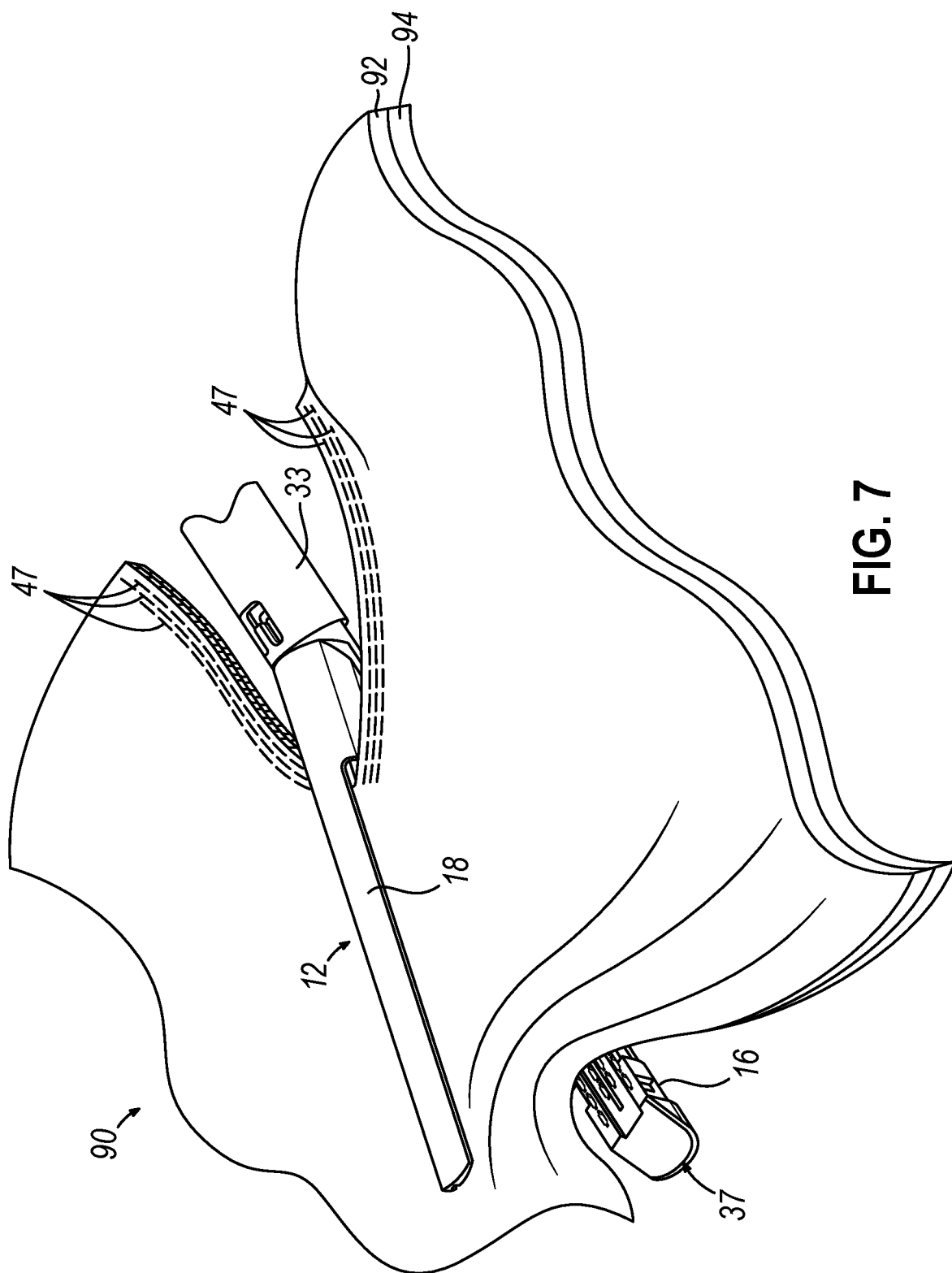
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly and Buttress Applier Cartridge

In some instances, it may be desirable to equip end effector (12) of surgical instrument (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

Figure 8:
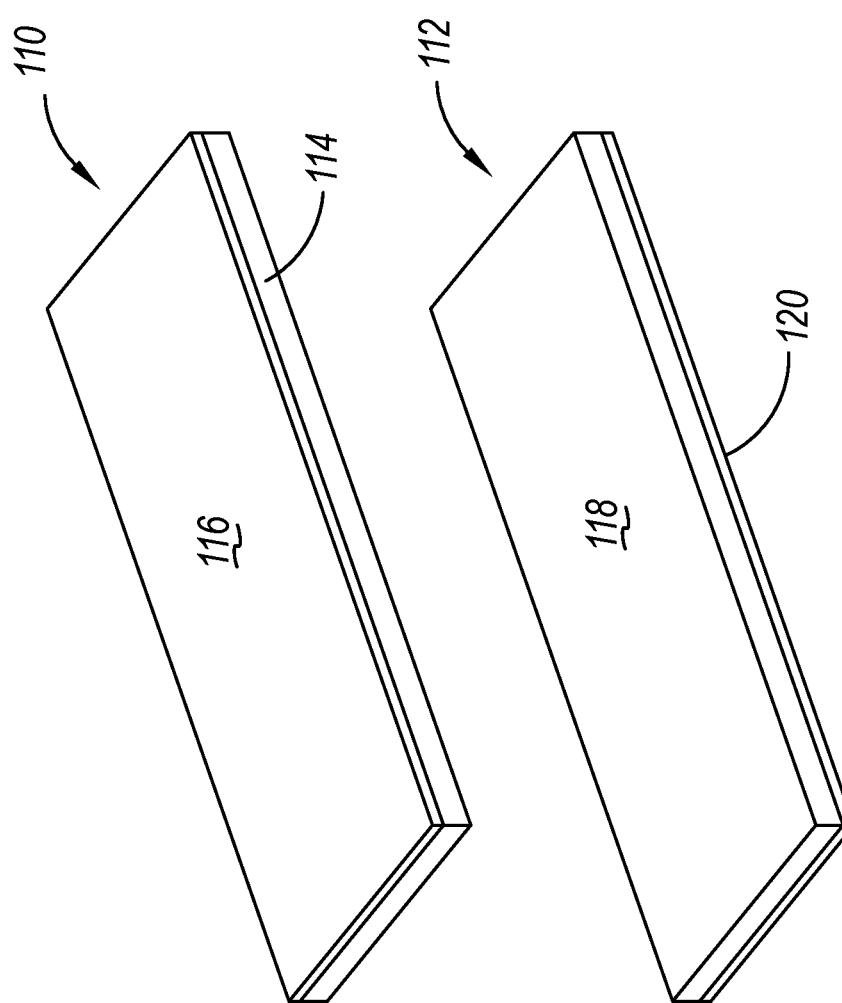
FIG. 8 depicts a perspective view of an exemplary pair of buttress assemblies, each of which may be applied to a jaw of the end effector of FIG. 3.

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
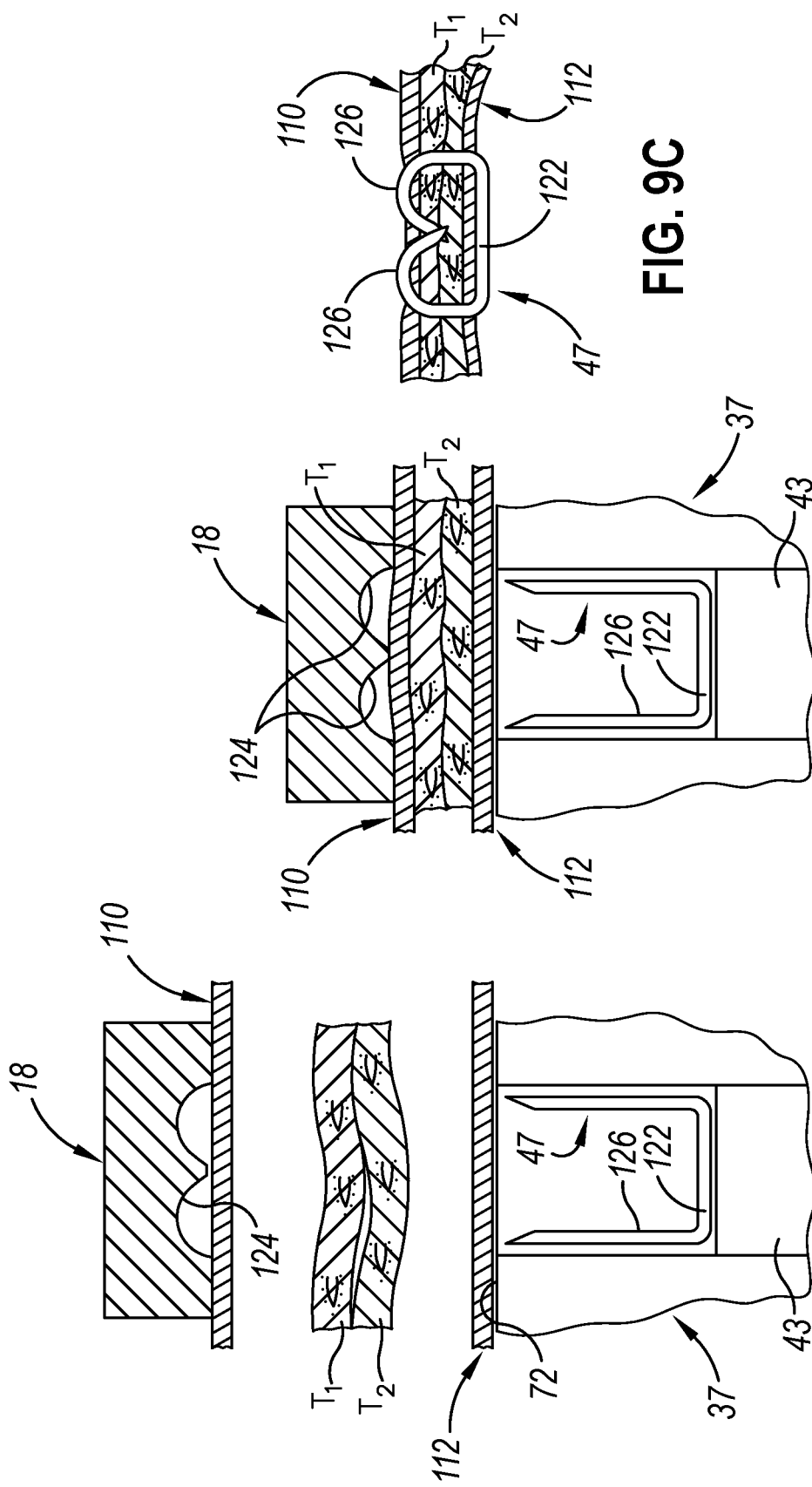
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which surgical stapler end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in the open position. Buttress assembly (110) is adhered to underside (124) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
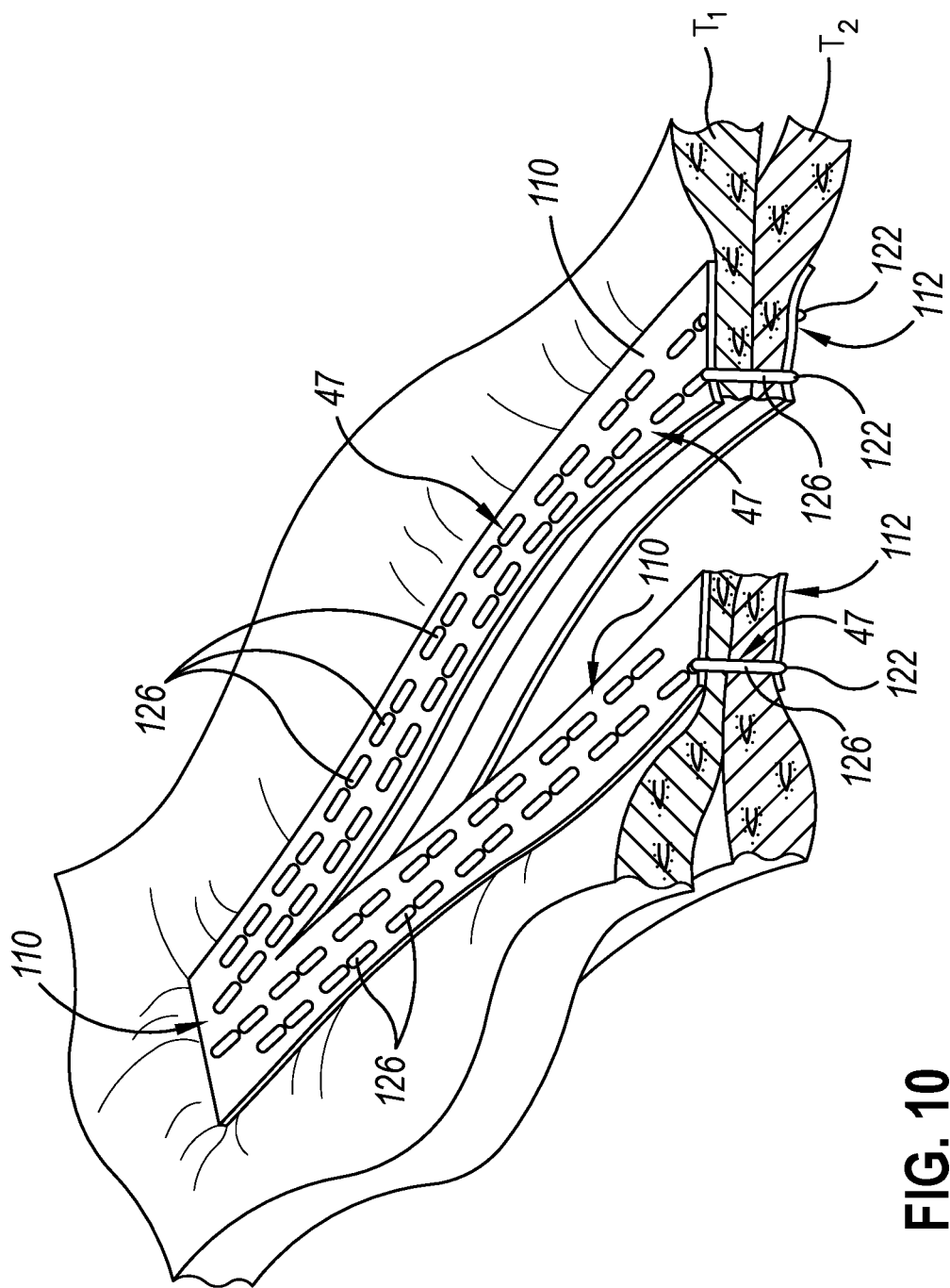
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttresses (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress tissue assemblies (110, 112), separating each buttress assembly (110, 112) into a corresponding pair of sections, such that each section remains secured to a respective severed region of tissue ($T_1$, $T_2$).

C. Exemplary Buttress Applier Cartridge with Active Retainer Arms

Figure 11:
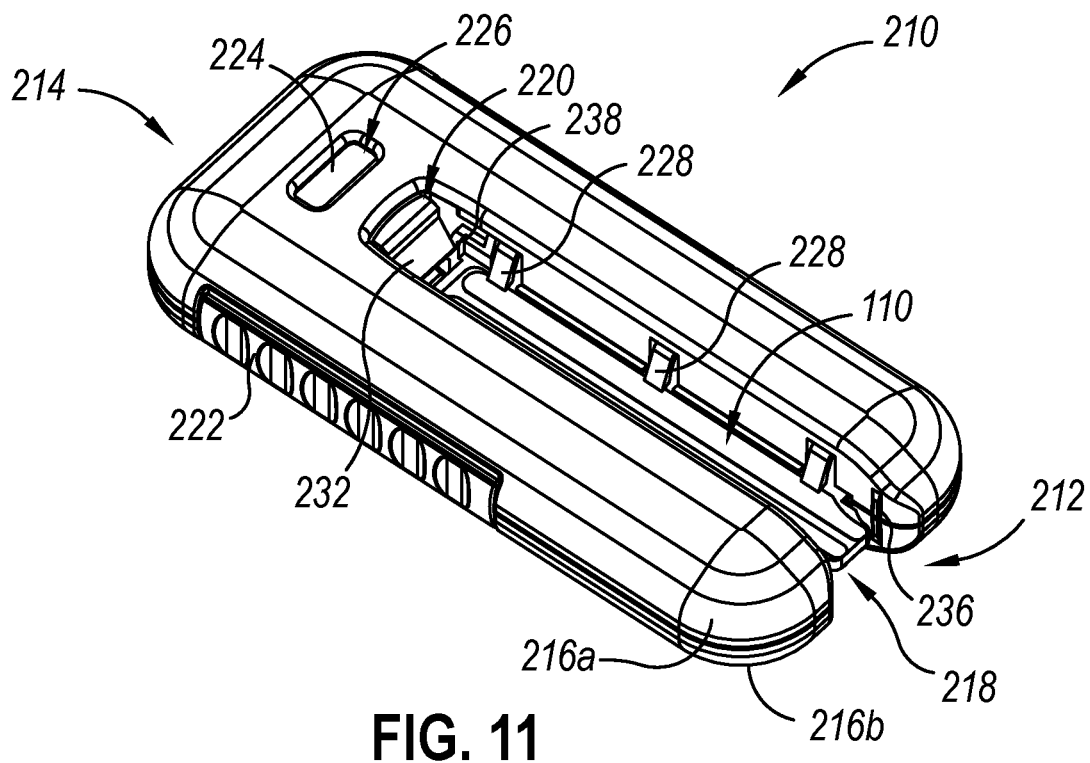
FIG. 11 depicts a perspective view of an exemplary buttress applier cartridge that may be used to carry and apply the buttress assemblies of FIG. 8.
Figure 12:
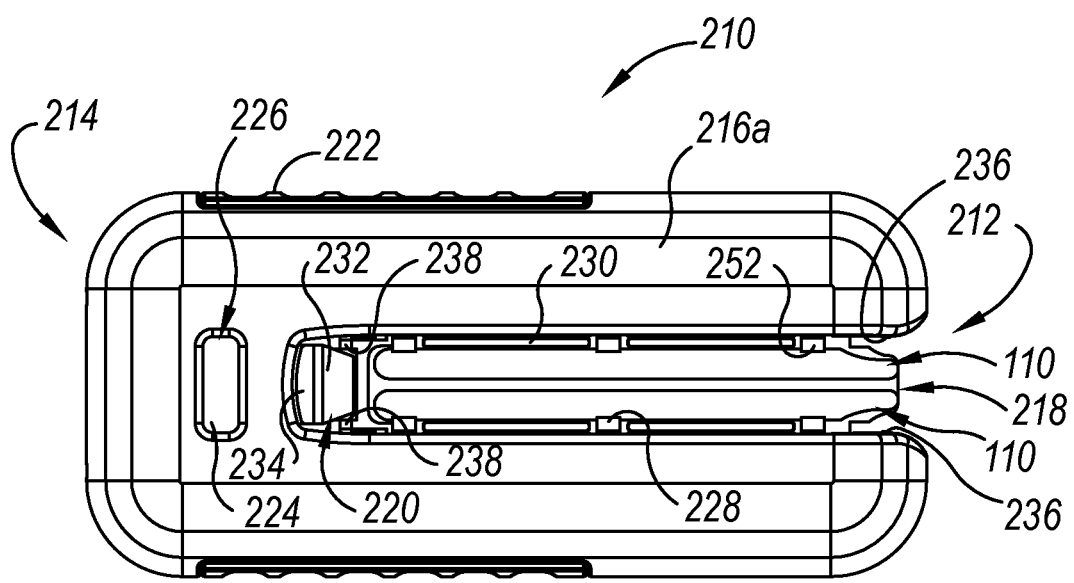
FIG. 12 depicts a top plan view of the buttress applier cartridge of FIG. 11.

Because end effector (12) of surgical instrument (10) may be actuated multiple times during a single surgical procedure, it may be desirable to enable an operator to repeatedly and easily load buttress assemblies (110, 112) onto end effector jaws (16, 18) during that single surgical procedure. FIGS. 11-13B show an exemplary buttress applier cartridge (210) (also referred to as a "buttress applicator") that may be used to support, protect, and apply adjunct material, such as buttress assemblies (110, 112), to end effector (12). As best seen in FIGS. 11-12, cartridge (210) of this example comprises an open end (212) and a closed end (214). Open end (212) is configured to receive end effector (12) as will be described in greater detail below. Cartridge (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, the outer edges of platform (218) include retention features (530) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Buttress applier cartridge (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with cartridge (210).

Figure 13A:
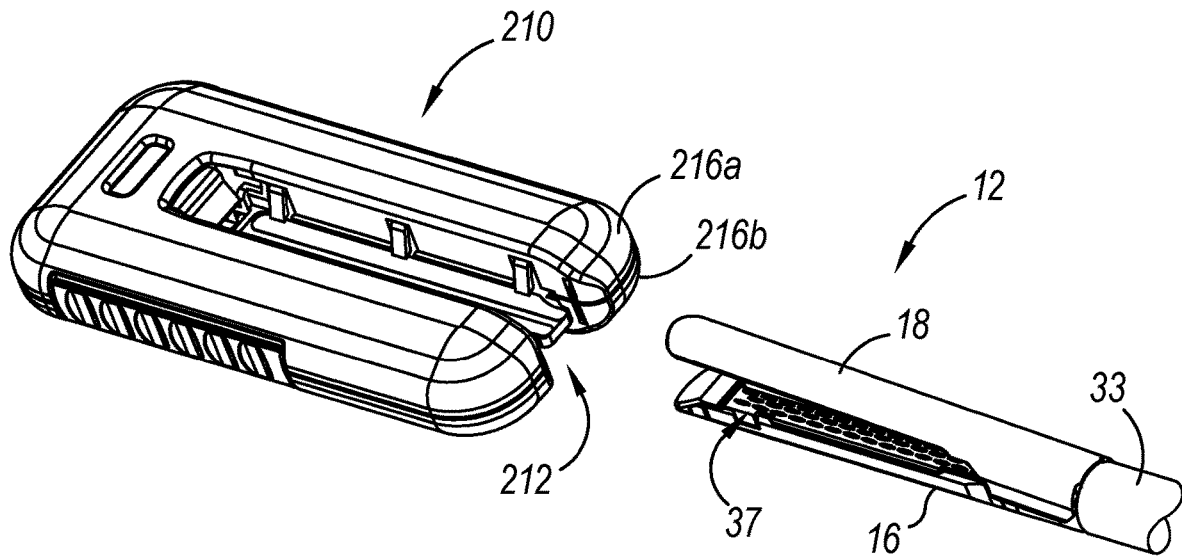
FIG. 13A depicts a perspective view of the end effector of FIG. 3 and the buttress applier cartridge of FIG. 11, showing the end effector and the buttress applier cartridge being aligned with one another.
Figure 13B:
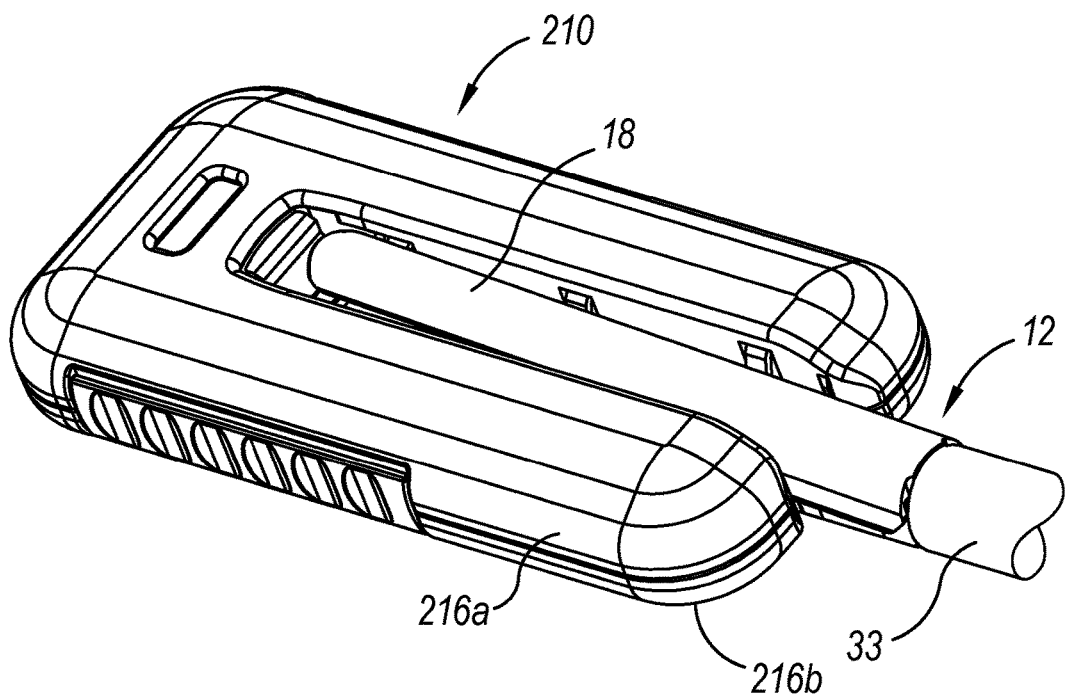
FIG. 13B depicts a perspective view of the end effector of FIG. 3 and the buttress applier cartridge of FIG. 11, with the end effectors jaws closed on a platform of the buttress applier cartridge.

FIG. 13A shows cartridge (210) in a configuration where retainer arms (228) are positioned to hold buttress assemblies (110, 112) against platform (218); while FIG. 13B shows cartridge (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use cartridge (210) to load end effector (12), the operator would first position cartridge (210) and end effector (12) such that end effector is aligned with open end (212) of cartridge (210) as shown in FIG. 13A. The operator would then advance end effector (12) distally, and/or advance cartridge (210) proximally, to position platform (218) and buttress assemblies (110, 112) between anvil (18) and staple cartridge (37) as shown in FIG. 13B. Closure trigger (26) of instrument (10) is then squeezed by the operator to close end effector jaws (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that end effector jaws (16, 18) may be disengaged from platform (218) while buttress assemblies (110, 112) remain adhered to anvil (18) and staple cartridge (37).

III. Exemplary Alternative Applicator Devices with Authentication Features and Related Methods of Applying a Buttress to a Surgical Stapler End Effector In some instances, it may be desirable to provide an applicator device that is configured to apply a staple reinforcing adjunct element to one or both jaws of a surgical stapler end effector while the jaws remain in an open state, or otherwise without closing the jaws via actuation of the stapler's end effector closure system, such as via actuation of closure trigger (26) of surgical stapler (10). The exemplary applicator devices described below provide such functionality, such that each applicator device is configured to be manipulated relative to an end effector to apply an adjunct element to one or both jaws without requiring actuated closure of the jaws like that shown in FIGS. 13A-13B described above. Additionally, the exemplary applicator devices described below may be operable to apply a minimum pressure to appropriately seat the adjunct material on the desired jaw (e.g., lower jaw (16) or anvil (18)).

In addition, in such examples, it may also be desirable for such applicator devices to include certain features to promote alignment between the applicator device and the jaws of the end effector. Such features may additionally, or in the alternative, be used to prevent reuse of such applicator devices, the end effector, or both. Such features may additionally, or in the alternative, be used to authenticate such applicator devices with a given end effector to promote use of such applicator devices with only a specific predetermined end effector or end effectors having a specific predetermined configuration.

It will be appreciated that any of the exemplary applicator devices described below may be configured to apply an adjunct element in the form of a buttress, such as buttresses (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of a staple reinforcement element to an end effector jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein. Furthermore, any of the exemplary applicator devices described below may be suitably constructed for a single use or for multiple uses.

A. Exemplary Alternative Applicator Device with Lockout

Figure 14A:
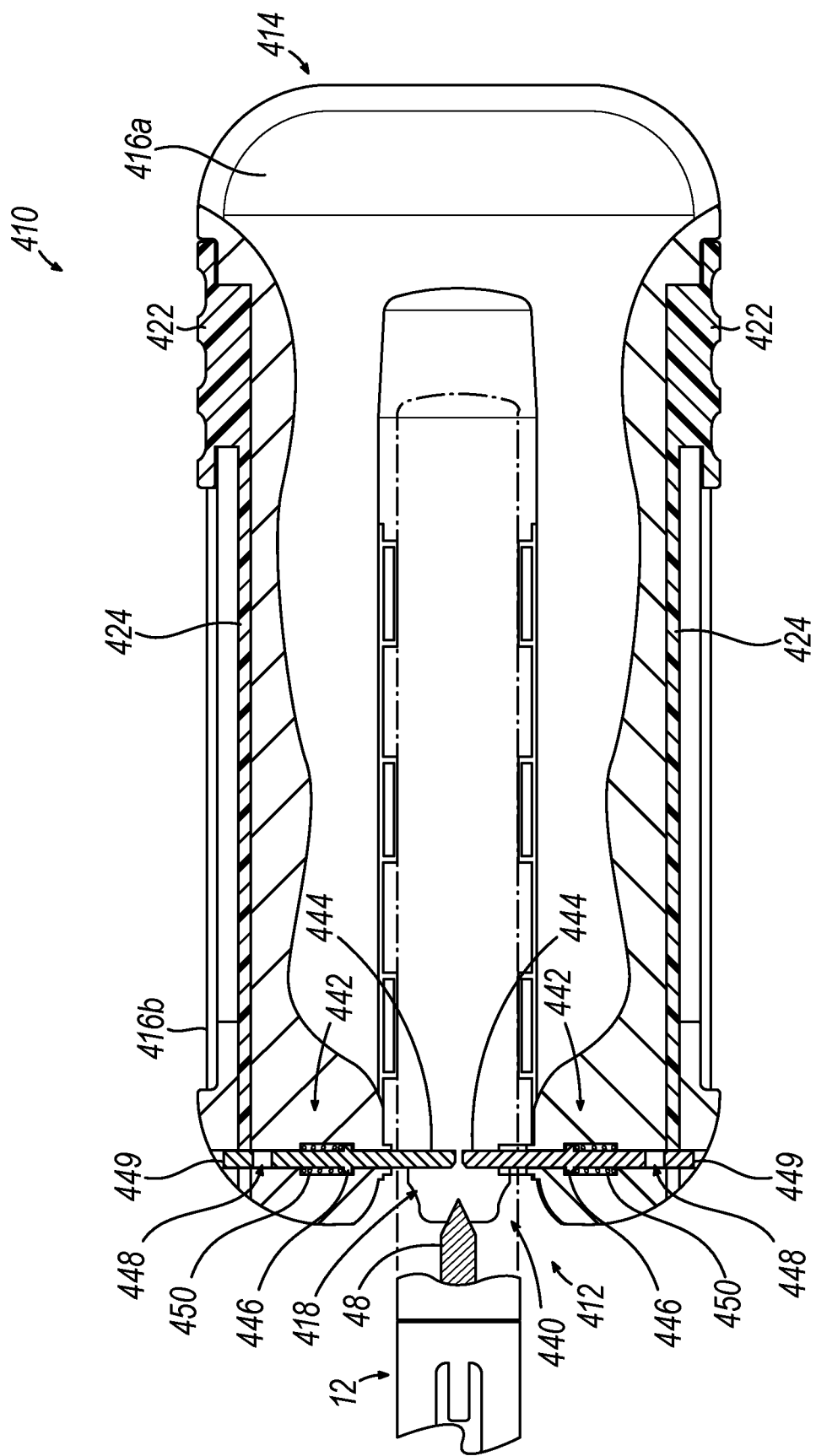
FIG. 14A depicts a top cutaway view of another exemplary buttress applier cartridge that may be used to carry and apply the buttress assemblies of FIG. 8, with the buttress applier cartridge in a locked configuration.

FIG. 14A shows an exemplary alternative buttress applier cartridge (410) (also referred to as a "buttress applicator") that may be used to support, protect, and apply adjunct material, such as buttress assemblies (110, 112), to end effector (12). Buttress applier cartridge (410) of the present example is substantially similar to buttress applier cartridge (210) described above except where otherwise explicitly described herein. For instance, as with cartridge, cartridge (410) of this example comprises an open end (412) and a closed end (414). As with open end (212) described above, open end (412) of this example is configured to receive end effector (12) as will be described in greater detail below. Similarly, cartridge (410) of this example further includes a first housing (416a) and a second housing (416b), which each collectively generally define a "U" shape to present open end (412). A platform (418) is similarly interposed between first and second housings (416a, 416b).

As with platform (218) described above, platform (418) of the present example is configured to support a pair of buttress assemblies (110) on one side of platform (418) and another pair of buttress assemblies (112) on the other side of platform (418). Platform (418) is exposed in recesses that are formed between the prongs of the "U" configuration of first and second housings (416a, 416b). Each buttress assembly (110, 112) is provided in a respective pair of portions that are separated to avoid spanning across slots (42, 49) of anvil (18) and staple cartridge (37), respectively, though platform (418) may just as easily support wide versions of buttress assemblies (110, 112) that unitarily span across slots (42, 49) of anvil (18) and staple cartridge (37), respectively.

Unlike platform (218) described above, platform (418) of this example is generally configured to expand in one or more directions for application of buttress assemblies (110, 112). As will be described in greater detail below, this functionality may be achieved by platform (418) operating as an expandable wedge. By way of example only, this functionality can be accomplished in some examples by configuring platform (418) or other suitable features of cartridge (410) in accordance with the teachings of U.S. Pat. App. Ser. No. 17/022,209, entitled "Apparatus and Method to Apply Buttress to End Effector of Surgical Stapler via Driven Member," filed on Sep. 16, 2020, the disclosure of which is incorporated by reference herein.

As with cartridge (210) described above, first and second housings (416a, 416b) include gripping features (422). However, unlike gripping features (222) described above, gripping features (422) of the present example are movable to selectively expand platform (418). As will be described in greater detail below, gripping features (422) are generally configured for translation relative to housings (416a, 416b) to thereby activate expansion of platform (418). As will also be described in greater detail below, it should be understood in certain configurations, gripping features (422) can be locked to prevent expansion of platform or otherwise lockout application of buttress assemblies (110, 112) using cartridge (410).

Unlike cartridge (210) described above, cartridge (410) of the present example includes a lockout assembly (440) disposed within housings (416a, 416b). Lockout assembly (440) is generally configured to prevent expansion of platform (418) until cartridge (410) is properly positioned within end effector (12) to thereby prevent misapplication of buttress assemblies (110, 112). In other words, lockout assembly (440) is generally configured to permit deployment of buttress assemblies (110, 112) only when a predetermined portion of end effector (12) engages lockout assembly (440). Such engagement can then be used to permit movement of gripping features (422) to activate expansion or other movement of platform (418).

Lockout assembly (440) of the present example is positioned proximate open end (412) and includes two actuators (442) extending inwardly into open end (412) from either side of cartridge (410) thereof. Each actuator (442) includes an engagement portion (444), a spring collar (446), a release opening (448), and a lock end (449). Although not shown, it should be understood that each actuator (442) in the present example is configured as an elongate rod, I-beam, or other elongate structure. Of course, various other suitable cross-sectional shapes may be used for each actuator (442) as will be apparent to those of ordinary skill in the art in view of the teachings herein.

Engagement portion (444) of each actuator (442) defines a length suitable for extending into open end (412) from housings (416a, 416b). In the present example, this length of extension for each engagement portion (444) is generally equivalent to half of the lateral length of open end (412). Thus, engagement portions (444) of each actuator (442) extend towards each other to collectively occupy the entire lateral length of open end (412). Alternatively, engagement portions (444) of each actuator (442) may collectively occupy most of the lateral length of open end (412) to define a slight gap at the end of each engagement portion (444). As will be described in greater detail below, such a gap between engagement portions (444) may be desirable to promote movement of each actuator (442) through engagement with a portion of end effector (12).

Spring collar (446) is positioned along the length of each actuator (442) between a respective engagement portion (444) and release opening (448). Spring collar (446) is generally configured to engage a spring (450) disposed within one or more of housings (416a, 416b) to bias each actuator (442) towards a predetermined position. In the present example, the combination of spring collar (446) and spring (450) is configured to bias each actuator (442) towards a locked position corresponding to the configuration shown in FIG. 14A. As will be described in greater detail below, each actuator (442) is positioned to prevent movement of a corresponding gripping feature (442) when in the locked position.

Release opening (448) is defined within each actuator (442) proximate lock end (449). As will be described in greater detail below, release opening (448) is generally configured to receive a portion of a corresponding gripping feature (422). To facilitation such a configuration, each release opening (448) corresponding to each actuator (442) extends through actuator (442) from one side to another. Thus, each release opening (448) is configured as a through hole extending through a corresponding actuator (442).

Adjacent to release opening (448), lock end (449) of each actuator (442) is positioned on the outermost end thereof. Each lock end (449) is generally configured to block movement of a portion of a corresponding gripping feature (422). Thus, it should be understood that lock end (449) is of a generally solid configuration. As will be described in greater detail below, each actuator (442) is generally configured to transition laterally within cartridge (410) to transition engagement between a portion of gripping feature (422) and lock end (449), or the portion of gripping feature (422) and release opening (448).

To promote engagement between gripping features (422) and lock assembly (440), each gripping feature (422), each gripping feature (422) includes a lock arm (424). In particular, each lock arm extends axially or proximally through cartridge (410) from a body of each gripping feature (422) towards each actuator (442). Each lock arm (424) is generally configured as an elongate rod or beam having a cross-section corresponding to the shape of a respective release opening (448). As will be described in greater detail below, each lock arm (424) is configured for receipt within a respective release opening (448) to permit movement of gripping feature (422).

Figure 14B:
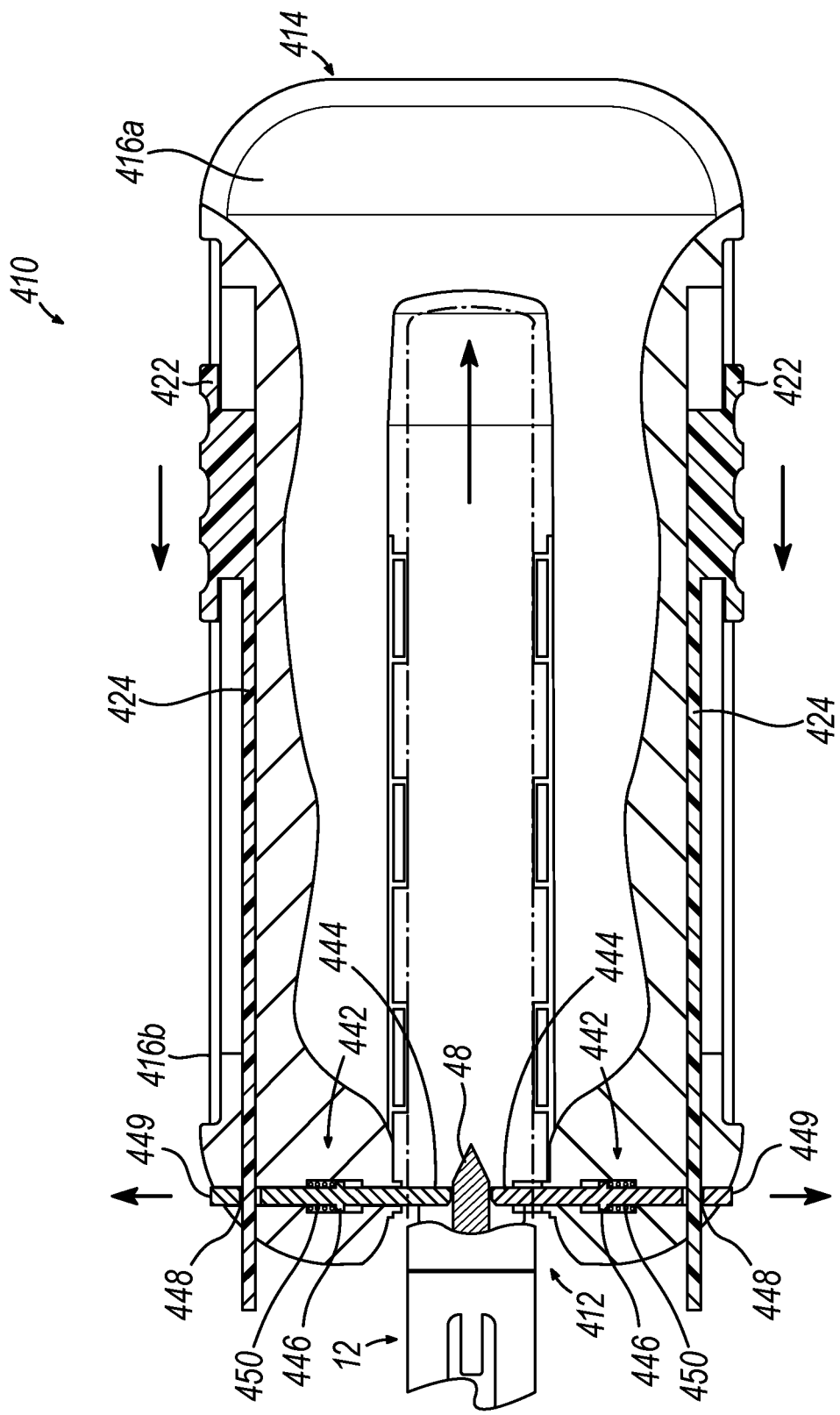
FIG. 14B depicts another top cutaway view of the buttress applier cartridge of FIG. 14A, showing the buttress applier cartridge in an unlocked configuration.

As best seen in FIGS. 14A and 14B, lockout assembly (440) is generally responsive to a predetermined portion of end effector (12) to lock and unlock movement of gripping features (422). As can be seen in FIGS. 15A and 15B, the unlocking movement of gripping features (422) permits activation of cartridge (410) by gripping features (422) to expand platform (418). Thus, lockout assembly (440) is configured to transition from a locked configuration shown in FIG. 14A to an unlocked configuration in FIG. 14B. This transition results in griping features (422) being usable to activate expansion of platform (418), as can be seen in FIG. 15B.

As can be seen in FIG. 14A, in the locked configuration, each actuator (442) of lockout assembly (440) is positioned inwardly such that each engagement portion (444) is nearly in contact (or alternatively in contact) with the opposite engagement portion (444). Correspondingly, each lock end (449) is positioned adjacent to a proximal end of a corresponding lock arm (424). Thus, each lock end (449) blocks movement of each gripping feature (442) via lock arm (424)

when lockout assembly (440) is in the locked configuration. Additionally, it should be understood that lockout assembly (440) is biased by spring (450) and spring collar (446) towards the locked configuration.

Transition of lockout assembly (440) from the locked configuration to the unlocked configuration is shown in FIG. 14B. As can be seen, the transition of lockout assembly (440) is driven by a predetermined portion of end effector (12). In the present example, this transition is driven by cutting edge (48) of end effector (12). Use of cutting edge (48) in the present example is generally desirable because the particular shape, size, and position of cutting edge (48) can be unique to end effector (12). Thus, use of cutting edge (48) as described herein can function as a lockout feature to promote use of cartridge (410) with only certain specific end effectors corresponding to end effector (12) described above. In other words, end effectors having a different configuration than end effector (12) described above may not be useable with cartridge (410). The use of cutting edge (48) as described herein is further desirable to prevent deployment of buttress assemblies (110, 112) until cartridge (410) is properly positioned within end effector (12). Although cutting edge (48) is shown and described herein as being usable to drive lockout assembly (440), it should be understood that in other examples, various alternative portions of end effector (12) can be used to drive the transition of lockout assembly (440). As will be understood, suitable portions of end effectors (12) may include any portion of end effector (12) that is unique or varied relative to other end effector configurations or styles.

Returning to the present example, lockout assembly (440) is transitioned by engagement between engagement portion (444) of each actuator (442) with cutting edge (48) of end effector (12). In particular, cartridge (410) is inserted into/onto end effector (12) (or end effector (12) is inserted into/onto cartridge (410)) to bring cutting edge (48) into contact with each engagement portion (444). This contact pushes each actuator (442) outwardly away from the opposite actuator (442) by a predetermined distance. Once this predetermined distance is reached as shown in FIG. 14B, each release opening (448) is positioned adjacent to the proximal end of a corresponding lock arm (424). This permits each lock arm (424) to be received within a corresponding release opening (448). As a result, each gripping feature may be translated proximally relative to housings (416a, 416b).

As shown in FIG. 15B, once lockout assembly (440) is transitioned to the unlocked configuration, each gripping feature (422) can be moved proximally to activate expansion of platform (418). This expansion pushes platform (418) towards upper deck (72) and anvil (18) of end effector (12) for deployment of buttress assembly (110, 112) thereon. Although not shown, it should be understood that gripping features (422) can be in communication with one or more features suitable to activate expansion of platform (418). In the present example, gripping features (422) are used to drive a linkage assembly to expand platform (418). As discussed above, expansion of platform (418) can be accomplished using a variety of mechanical and/or electrical configuration.

B. Exemplary Alternative Applicator Device with Keyed Release

Figure 16:
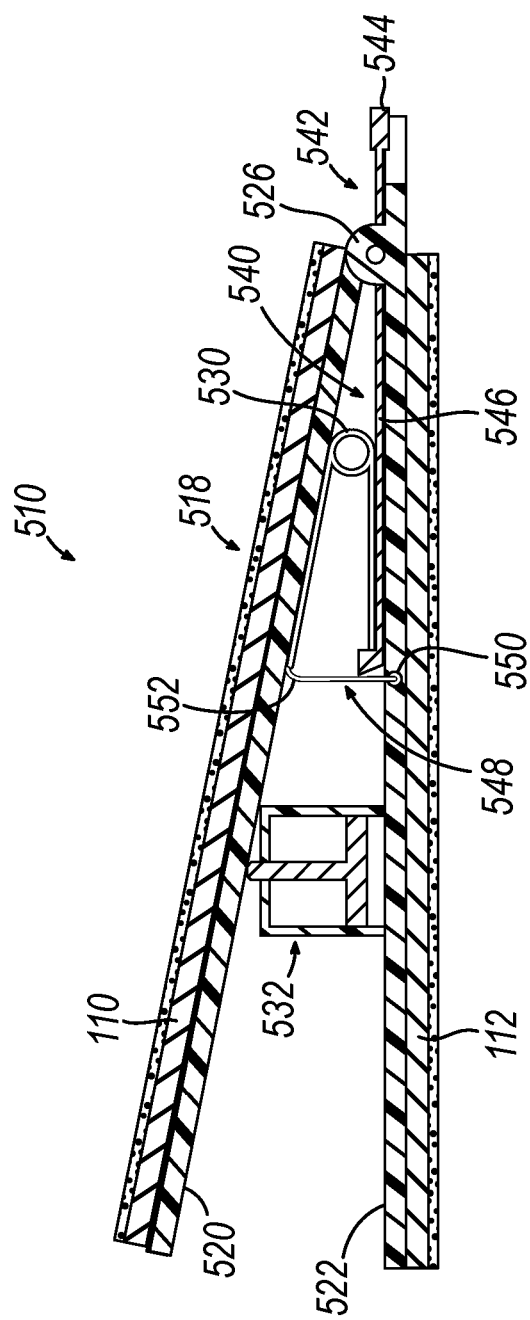
FIG. 16 depicts a side cross-sectional view of yet another buttress applier cartridge that may be used to carry and apply the buttress assemblies of FIG. 8.

FIG. 16 shows another exemplary buttress applier cartridge (510) (also referred to as a "buttress applicator") that may be used to support, protect, and apply adjunct material, such as buttress assemblies (110, 112), to an end effector. Buttress applier cartridge (510) of the present example is substantially similar to buttress applier cartridge (210, 410) described above except where otherwise explicitly described herein. For instance, as with cartridge (410), cartridge (510) of this example comprises a housing (not shown) defining an open end (not shown) and a closed end (not shown). A platform (518) is similarly interposed between one or more portions of the housing.

As with platform (418) described above, platform (518) of the present example is configured to support a pair of buttress assemblies (110) on one side of platform (518) and another pair of buttress assemblies (112) on the other side of platform (518). Also as with platform (418), platform (518) of the present example is generally configured to be expandable to apply buttress assemblies (110, 112). To support such expandability, platform (518) includes an upper support (520), and a lower support (522) connected with a hinge (526). Upper support (520) comprises an elongate flat surface configured for support of buttress assembly (110). Meanwhile, lower support (522) also comprises an elongate flat surface configured for support of buttress assembly (112).

Upper support (520) is connected to lower support (522) at hinge (526). Hinge (526) is positioned at the proximal end of each support (520, 522) such that hinge (526) is generally configured for insertion into an end effector (612), as will be described in greater detail below. Hinge (526) is generally configured to permit pivoting of upper support (520) relative to lower support (522).

Platform (518) of the present example is configured to expand automatically (e.g., without an operator pushing or pulling portions of platform (518)). To facilitate such automatic expansion, platform (518) of the present example further includes a resilient member or torsion spring (530) and a dashpot (532). Torsion spring (530) is configured to provide an outward force against upper support (520) and lower support (522) to bias platform (518) towards an expanded configuration. Meanwhile, dashpot (532) is generally configured to provide a controlled force opposite of torsion spring (530) (e.g., an inwardly oriented force). As will be understood, dashpot (532) is generally configured to act as a damper to prevent torsion spring (530) from expanding platform (518) at an undesirable rate. By way of example only, this functionality can be accomplished in some examples by configuring platform (518) or other suitable features of cartridge (510) in accordance with the teachings of U.S. Pat. App. Ser. No. 17/022,209, entitled "Apparatus and Method to Apply Buttress to End Effector of Surgical Stapler via Driven Member," filed on Sep. 16, 2020, the disclosure of which is incorporated by reference herein.

To activate expansion of platform (518), cartridge (510) of the present example further includes a release assembly (540). Release assembly (540) is generally configured to engage a predetermined portion of end effector (612) to activate expansion of platform (518) upon such engagement. Thus, release assembly (540) is similar to lockout assembly (440) described above in that release assembly (540) promotes use of cartridge (510) with only certain end effectors and also promote activation of cartridge (510) only when cartridge (510) is properly positioned within such end effectors.

Release assembly (540) of the present example comprises a probe (542) and a latch (548). Probe (542) includes a keyed end (544) and an elongate pusher (546) extending from keyed end (544). A portion of probe (542) extends proximally from hinge (526) such that keyed end (544) protrudes from a proximal end of cartridge (510). As will be described in greater detail below, the particular position of probe (542)

is configured to permit engagement between keyed end (544) and a predetermined portion of end effector (610) when lower support (522) is properly seated within end effector (612).

Elongate pusher (546) extends distally from hinge (526) and keyed end (544) towards torsion spring (530) and latch (548). Elongate pusher (546) is generally responsive to movement of keyed end (544) such that movement of keyed end (544) results in corresponding movement of elongate pusher (546). As will be described in greater detail below, movement of elongate pusher (546) is configured to actuate latch (548), which releases torsion spring (530) and thereby expanding platform (518).

Latch (548) is generally configured to selectively engage torsion spring (530) to hold torsion spring (530) in a compressed configuration. In the present example, latch (548) comprises an elongate rod, or wire that includes coupler (550) and a release (552). Coupler (550) is pivotably coupled to lower support (522) to permit latch (548) to pivot relative to lower support (522). Release (552) is positioned opposite of coupler (550) as is configured to releasably engage torsion spring (530) and/or a portion of upper support (520) to hold torsion spring (530) in the compressed configuration. As will be described in greater detail below, elongate pusher (546) is generally configured to engage latch (548) to pivot latch (548) about coupler (550) to disengage release (552) from torsion spring (530) and/or a portion of upper support (520).

Although release assembly (540) is shown as having a specific configuration, it should be understood that in other examples, a variety of alternative configurations may be used. For instance, in some examples other mechanical release mechanisms can be used to permit selective expansion of platform (518) via torsion spring (530) or other mechanisms configured for storage of potential energy. In other examples, release assembly (540) can use various electrical/mechanical components such as solenoids, motors, push-buttons, sensors, and/or etc. Of course, still various other suitable configurations for release assembly (540) as will be apparent to those of ordinary skill in the art in view of the teachings herein.

Figure 17A:
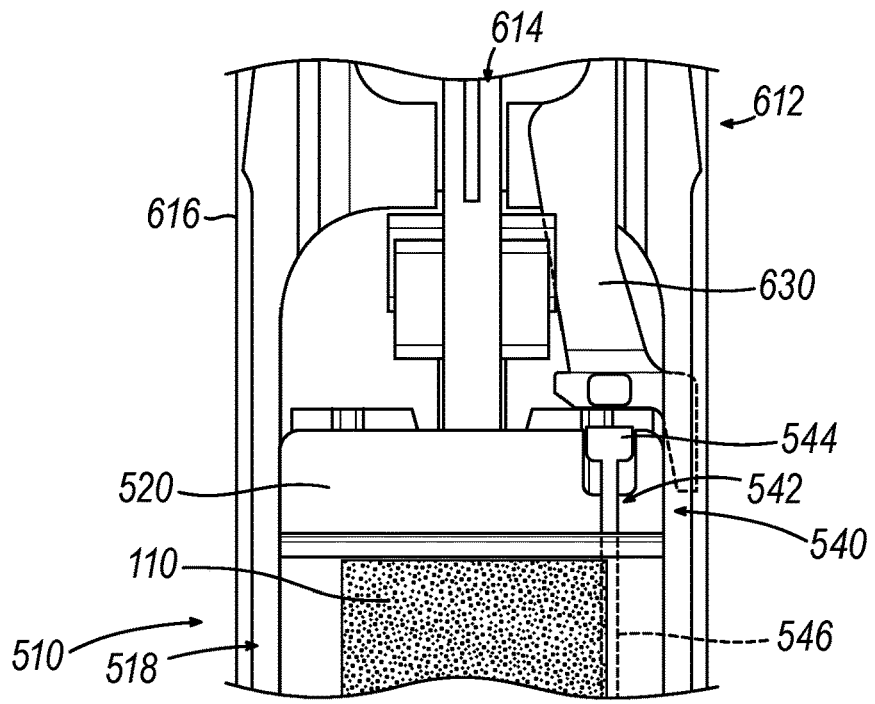
FIG. 17A depicts a top detailed plan view of the buttress applier cartridge of FIG. 16, with an end effector being inserted into the buttress applier cartridge and having select components omitted from view.

As can be seen in FIG. 17A, cartridge (510) of the present example is configured for use with end effector (612). End effector (612) of the present example is substantially similar to end effector (12) described above except where otherwise explicitly noted herein. For instance, like with end effector (12) described above, end effector (612) of the present example employs a firing beam (614) that may be used to sever and staple tissue in a single stroke. As with firing beam (14) described above, firing beam (614) of the present example may be driven relative to an anvil (not shown) (similar to anvil (18)) and an unspent staple cartridge (not shown) (similar to staple cartridge (37)) to sever and staple tissue. As with staple cartridge (37), the staple cartridge of end effector (612) is removably installed into a channel of a lower jaw (616).

Unlike end effector (12) described above, end effector (612) of the present example includes a cartridge lockout (630) integrated into end effector (612). Lockout (630) is generally configured to mate with certain corresponding components of a staple cartridge. Such a mating arrangement moves lockout (630) into a predetermined position and unlocks certain operations of end effector (612) such as movement of firing beam (614) and closure of the anvil. Thus, it should be understood that lockout (630) is configured to prevent use of end effector (612) when no staple cartridge is installed, an improper (e.g., lacking mating features) staple cartridge is installed, or a staple cartridge is improperly installed. In some examples, lockout (630) and other associated features of end effector (612) and the staple cartridge can be configured in accordance with the teachings of U.S. patent application Ser. No. 16/453,273, entitled "Method for Providing an Authentication Lockout in a Surgical Stapler with a Replaceable Cartridge," filed on Jun. 26, 2019, the disclosure of which is incorporated by reference herein.

Figure 17B:
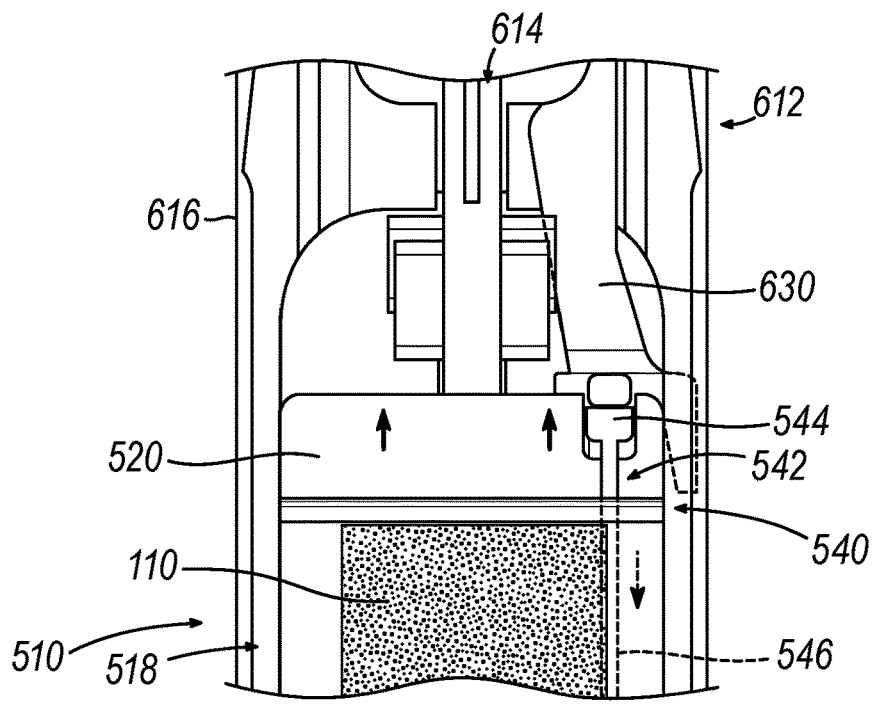
FIG. 17B depicts another top detailed plan view of the buttress applier cartridge of FIG. 17, with the end effector of FIG. 17A fully inserted into the buttress applier cartridge and having select components omitted from view.
Figure 18:
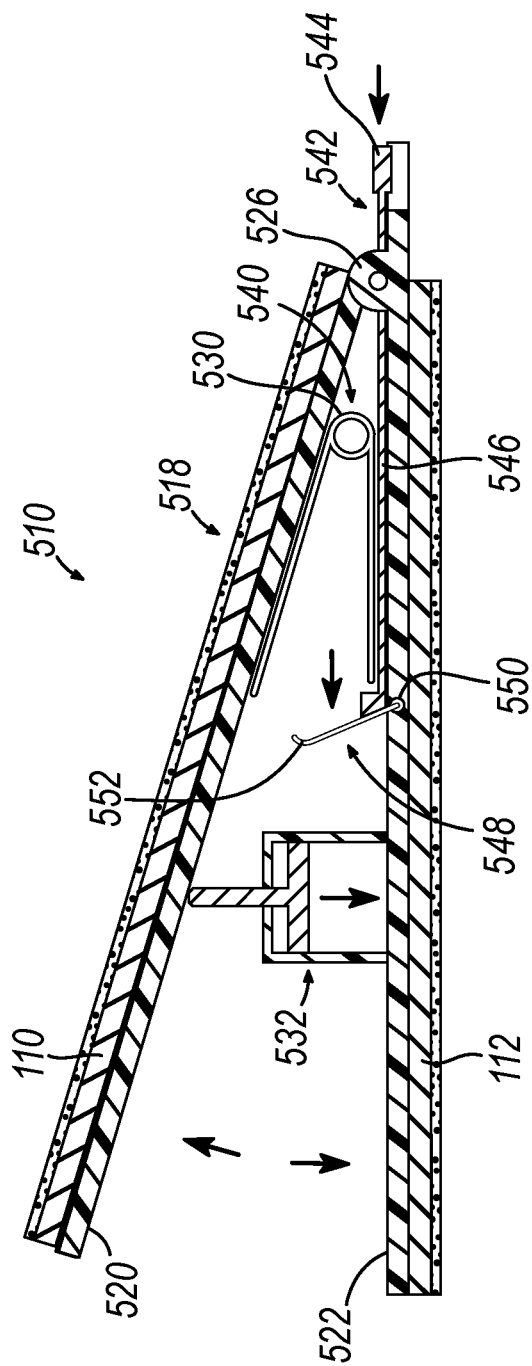
FIG. 18 depicts another side cross-sectional view of the buttress applier cartridge of FIG. 16, with a platform of the buttress applier cartridge in an expanded configuration.

Use of buttress applier cartridge (510) with end effector (612) is shown in FIGS. 17A through 18. As can be best seen in FIG. 17A, cartridge (510) may be first inserted into end effector (612) to position lower support (522) into alignment with lower jaw (616) of end effector (612). The direction of insertion is such that hinge (526) and keyed end (544) are inserted into end effector (612) first towards lockout (630).

Once cartridge (510) is fully inserted into end effector (612), keyed end (544) engages a portion of lockout (630) as can be seen in FIG. 17B. In some examples, the particular geometry of keyed end (544) may be configured to correspond to a specific geometric feature of lockout (630) to further promote precise positioning of cartridge (510) relative to end effector (612). Regardless, upon engagement between keyed end (544) and lockout (630), keyed end (544) pushes probe (542) distally.

As best seen in FIG. 18, upon distal movement of probe (542), elongate pusher (546) engages latch (548). Latch (548) is correspondingly pushed by elongate pusher (546) to pivot about coupler (550), thereby disengaging release (552) from torsion spring (530) and/or upper support (520). With torsion spring (530) released, platform (518) can expand at a controlled pace using the force applied by torsion spring (530) and dashpot (532) to apply buttress assemblies (110, 112) to end effector (612).

C. Exemplary Alternative Applicator Device with RFID Authentication

Figure 20A:
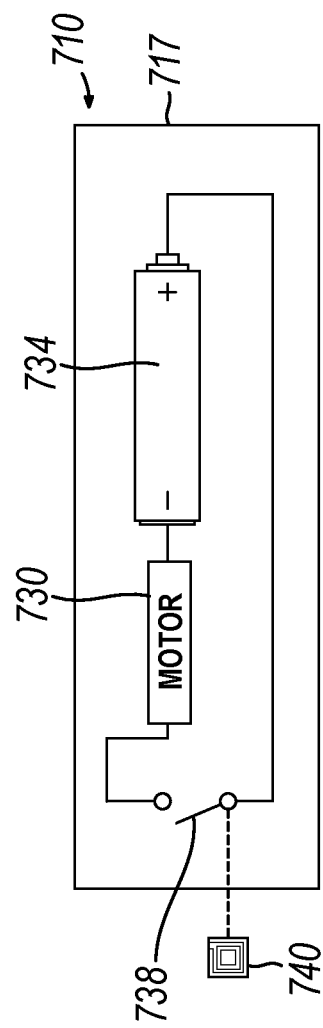
FIG. 20A depicts a schematic view of an interior of the buttress applier cartridge of FIG. 19A and a switch in an open circuit configuration.

FIGS. 19A and 20A depict yet another exemplary alternative buttress applier cartridge (710) (also referred to as a "buttress applicator") that may be used to support, protect, and apply adjunct material, such as buttress assemblies (110, 112), to an end effector. Buttress applier cartridge (710) of the present example is substantially similar to buttress applier cartridge (210, 410, 510) described above except where otherwise explicitly described herein. For instance, as with cartridge (410), cartridge (710) of this example comprises a housing (716) defining an open end (712) and a closed end (714). A platform (718) is similarly interposed between one or more portions of the housing.

As with platform (418) described above, platform (718) of the present example is configured to support a pair of buttress assemblies (110) on one side of platform (718) and another pair of buttress assemblies (112) on the other side of platform (718). Also as with platform (418), platform (718) of the present example is generally configured to be expandable to apply buttress assemblies (110, 112). To support such expandability, platform (718) includes certain mechanisms generally configured to promote expansion thereof. By way of example only, platform (718) of the present example includes an expandable wedge driven by a linkage mechanism similar to platform (418) described above. However, it should be understood that in other examples, other suitable mechanisms may be used such as an expandable balloon, a spring-loaded wedge, a lead screw driven mechanism, and/or etc. In still other examples, platform (718) may be configured in accordance with one or more of the teachings of U.S. Pat. App. Ser. No. 17/022,209, entitled "Apparatus and Method to Apply Buttress to End Effector of Surgical Stapler via Driven Member," filed on Sep. 16, 2020, the disclosure of which is incorporated by reference herein.

Unlike platform (418) described above, expandability of platform (718) in the present example is motor driven rather than being manually driven by an operator. In particular, as best seen in FIG. 20A, the interior of cartridge (710) includes a motor (730), a power source (734), and a switch (738), all incorporated into a circuit. Although not shown, it should be understood that motor (730) of the present example may be in communication with one or more features of platform (718) to drive expansion of platform (718). For instance, as noted above, platform (718) of the present example can use a linkage mechanism to provide expansion thereof. Thus, in such an example, motor (730) can be configured to rotate a lead screw or other drive mechanism to move platform (718) from a flat configuration to an expanded configuration. Of course, in other configurations where alternative expansion mechanisms are used, motor (730) may be varied as needed. For instance, in some examples motor (730) can include a vacuum pump, a linear actuator, and/or etc.

Switch (738) is in communication with motor (730) and power source (734) to selectively activate and deactivate power supplied to motor (730) via power source (734). Power source (734) of the present example is shown as a battery, although any other suitable source of power may be used including direct and/or alternating current sources. Although not shown, it should be understood that motor (730), power source (734) and switch (738) can be connected to other electrical circuitry such as microcontrollers, controllers, relays, diodes, capacitors, inductors, resistors, inverters, and/or etc.

Returning to FIG. 19A, cartridge (710) further includes an RFID module (740). As will be described in greater detail below, RFID module (740) is generally configured to respond to one or more corresponding RFID components of end effector (812). This relationship is generally desirable to provide both confirmation that cartridge (710) is used with a suitable end effector similar to end effector (810), and confirmation that cartridge (710) is properly positioned prior to deployment of buttress assemblies (110, 112) via platform (718).

As can be seen, RFID module (740) is in communication with switch (738). In the present example, RFID module (740) is configured to trip or otherwise actuate switch (738) between an open and closed circuit configuration. As will be understood, this configuration permits RFID module (740) to activate motor (730) and thereby expand platform (718) for deployment of buttress assemblies (110, 112) only when RFID module (740) is in proximity with certain corresponding features of end effector (812).

RFID module (740) of the present example is positioned adjacent to the proximal end of cartridge (710) proximate open end (712). Although only a single RFID module (740) is visible, it should be understood that an additional RFID module (740) may be disposed on each side of cartridge (710) (e.g., one on the side out of the page in FIG. 19A and one on the side into the page in FIG. 19A). As will be described in greater detail below, this proximal positioning is generally desirable to confirm proper positioning of cartridge (710) within end effector (812). In other examples, any suitable number of RFID modules (740) may be used. For instance, in some examples, four RFID modules (740) can be used with two on the proximal end of cartridge (710) and two on the distal end of cartridge (710). Such a configuration may be desirable to provide improved position confirmation. Thus, in other examples, even more RFID modules (740) may be used as will be apparent to those of ordinary skill in the art in view of the teachings herein. Additionally, it should be understood that in examples where multiple RFID modules (740) are used, all such RFID modules (470) may be in communication with switch (738) such that all RFID models (740) may be used to transition switch (738) between the open and closed circuit configurations.

As seen in FIG. 19A, cartridge (710) is usable with end effector (812). End effector (812) of the present example is substantially similar to end effector (12) described above except where otherwise explicitly noted herein. For instance, like with end effector (12) described above, end effector (812) of the present example employs a firing beam (814) that may be used to sever and staple tissue in a single stroke. As with firing beam (14) described above, firing beam (814) of the present example may be driven relative to an anvil (818) and an unspent staple cartridge (837) to sever and staple tissue. As with staple cartridge (37), staple cartridge (837) is removably installed into a channel of a lower jaw (816).

Unlike end effector (12) described above, end effector (812) of the present example includes an RFID module (840) positioned adjacent to the crotch formed by anvil (818) and lower jaw (816). RFID module (840) of end effector (812) is generally configured to communicate with RFID module (740) of cartridge (710). By way of example only, RFID module (840) of end effector (812) is configured as an RFID sensor or antenna. Meanwhile, RFID module (740) of cartridge (710) is configured as an RFID chip or transmitter for transmission of radio frequencies to RFID module (840) of end effector (812). Of course, in other examples, this configuration can be reversed and RFID module (840) can be configured as a chip or transmitter, while RFID module (740) can be configured as a sensor or antenna.

Although end effector (812) of the present example is shown as having a single RFID module (840), it should be understood that in other examples, end effector (812) can include any suitable number of RFID modules (840). For instance, in some examples, an array of RFID modules (840) can be used in end effector (812), with groups of RFID modules (840) being configured to serve certain specific purposes. In such configurations, one group of RFID modules (840) may be used to detect and authenticate the presence of a specific staple cartridge similar to staple cartridge (837). Meanwhile, another group of RFID modules (840) may be used to detect and authenticate the presence of a specific buttress applier cartridge similar to buttress applier cartridge (710). Still another group of RFID modules (840) may be used to detect other and authenticate the presence (or lack thereof) of other ancillary components such as staple cartridge retainer. In some examples, suitable configurations for RFID module (840) may be in accordance with at least some of the teachings of U.S. patent application Ser. No. 16/458,108, entitled "Surgical Instrument System Comprising an RFID System," filed on Jun. 30, 2019, the disclosure of which is incorporated by reference herein.

An exemplary use of the present example is shown in FIGS. 19A through 20B. As can be seen, end effector (812) is initially moved relatively to cartridge (710) to insert cartridge (710) into end effector (812). FIG. 20A shows switch (738) of cartridge (710) as being in the open configuration during insertion. This open configuration corresponds to platform (718) being in a non-expanded configuration. Although not shown, it should be understood that in some uses, end effector (812) may be electronically locked prior to and during insertion of cartridge (710). For instance, RFID module (840) may generate a signal corresponding to cartridge (710) not being detected. This signal may then be communicated with electronic circuitry within end effector (810) or other portions of the instrument (not shown) to physically or electronically lock portions of the instrument or end effector (810) from moving (e.g., to prevent distal advancement of firing beam (814)).

Figure 20B:
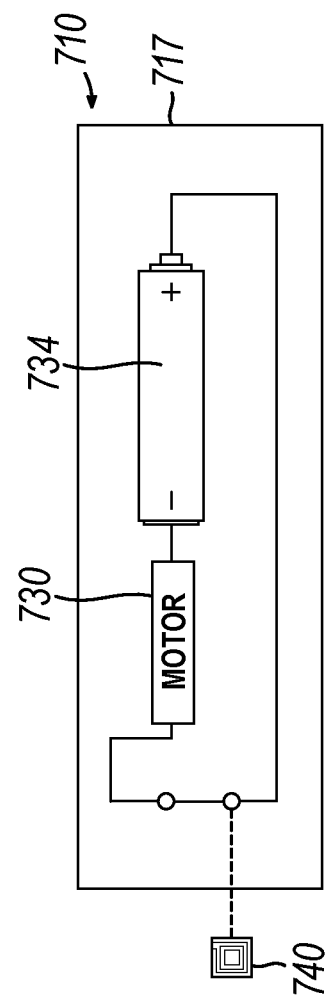
FIG. 20B depicts another schematic view of the interior of the buttress applier cartridge of FIG. 19A, showing the switch in a closed circuit configuration.

Once cartridge (710) is fully inserted into end effector (812), RFID module (740) of cartridge (710) is adjacent to RFID module (840) of end effector (812) as can be seen in FIG. 19B. RFID module (740) then responds to the presence of RFID module (840) by transitioning switch (738) from the open configuration to the closed configuration as shown in FIG. 20B. This transition of switch (738) causes motor (730) to activate and thereby expand platform (718), which results in application of buttress assemblies (110, 112) to anvil (818) and staple cartridge (837) of end effector (812).

In some uses, RFID module (840) may also respond to the presence of RFID module (740). For instance, RFID module (840) may generate one or more signals upon detection of the presence of RFID module (740). Such signals may then be transmitted to other portions of end effector (812) or the instrument to release or otherwise disengage certain lockout features. Alternatively, such lockout features may remain active, but may be disengaged after either a predetermined amount of time or until the presence of RFID module (740) is no longer detected.

D. Exemplary Alternative Applicator Device with External Power Input

FIG. 21A depicts yet another exemplary alternative buttress applier cartridge (910) (also referred to as a "buttress applicator") that may be used to support, protect, and apply adjunct material, such as buttress assemblies (110, 112), to an end effector. Buttress applier cartridge (810) of the present example is substantially similar to buttress applier cartridge (210, 410, 510, 710) described above except where otherwise explicitly described herein. For instance, as with cartridge (410), cartridge (910) of this example comprises a housing (916) defining an open end (912) and a closed end (914). A platform (918) is similarly interposed between one or more portions of housing (916).

As with platform (418) described above, platform (918) of the present example is configured to support a pair of buttress assemblies (110) on one side of platform (918) and another pair of buttress assemblies (112) on the other side of platform (918). Also as with platform (418), platform (918) of the present example is generally configured to be expandable to apply buttress assemblies (110, 112). To support such expandability, platform (918) includes certain mechanisms generally configured to promote expansion thereof. By way of example only, platform (918) of the present example includes an expandable wedge driven by a linkage mechanism similar to platform (418) described above. However, it should be understood that in other examples, other suitable mechanisms may be used such as an expandable balloon, a spring-loaded wedge, a lead screw driven mechanism, and/or etc. In still other examples, platform (918) may be configured in accordance with one or more of the teachings of U.S. Pat. App. Ser. No. 17/022,209, entitled "Apparatus and Method to Apply Buttress to End Effector of Surgical Stapler via Driven Member," filed on Sep. 16, 2020, the disclosure of which is incorporated by reference herein.

Unlike platform (418) described above, expandability of platform (918) in the present example is motor driven rather than being manually driven by an operator. In particular, as best seen in FIG. 21A, cartridge (910) includes a power input or keyed driver (930). Power input (930) is shown as being in communication with one or more features of platform (918) to drive expansion of platform (918). Such features of platform (918) can be driven by power input (930) in a variety of ways. For instance, as noted above, platform (918) of the present example can use a linkage mechanism to provide expansion thereof. Thus, in such an example, power input (930) can be configured to rotate a lead screw or other drive mechanism to move platform (918) from a flat configuration to an expanded configuration. Of course, in other configurations where alternative expansion mechanisms are used, power input (930) may be varied as needed. For instance, in some examples power input (930) can include a vacuum pump, a linear actuator, and/or etc.

Power input (930) is configured to communicate with certain features of an end effector (1012). As will be described in greater detail below, in some examples, end effector (1012) can include certain power output or rotary drive features that can be used to power, drive, or actuate certain accessory components configured for use with end effector (1012). Accordingly, it should be understood that cartridge (910) of the present example does not need an internal power source to operate. Instead, cartridge (910) can be driven by an external power source including, but not limited to, certain rotary drive components integrated into end effector (1012).

As seen in FIG. 21A, cartridge (910) is usable with end effector (1012). End effector (1012) of the present example is substantially similar to end effector (12) described above except where otherwise explicitly noted herein. For instance, like with end effector (12) described above, end effector (1012) of the present example employs a firing beam (1014) that may be used to sever and staple tissue in a single stroke. As with firing beam (14) described above, firing beam (1014) of the present example may be driven relative to an anvil (1018) and an unspent staple cartridge (1037) to sever and staple tissue. As with staple cartridge (37), staple cartridge (1037) is removably installed into a channel of a lower jaw (1016).

Unlike end effector (12) described above, end effector (1012) of the present example includes a power output or rotary driver (1040) positioned adjacent to the crotch formed by anvil (1018) and lower jaw (1016). Power output (1040) of end effector (1012) is generally configured to engage power input (930) of cartridge (910) to transfer power from end effector (1012) to cartridge (910). By way of example only, power output (1040) of the present example is configured to communicate rotary motion to cartridge (910) via power input (930). As best seen in FIG. 22, both power input (930) and power output (1040) are keyed relative to each other to facilitate communication of such rotary motion.

Although power input (930) and power output (1040) of the present example are configured for communication of mechanical rotary power, it should be understood that in other examples various forms of energy can be communicated between power input (930) and power output (1040). For instance, in some examples, power output (1040) may be configured to transmit translational motion to power input (930). In other examples, power output (1040) may be configured to transmit electrical, hydraulic, or pneumatic power to power input (930). In such examples, cartridge (910) can include other components suitable to use such electrical, hydraulic, or pneumatic power such as motors, pumps, valves, filters, and/or etc. Of course, in still other examples, various alternative power transfer mechanisms may be used as will be apparent to those of ordinary skill in the art in view of the teachings herein.

FIGS. 21A and 21B show an exemplary use of buttress applier cartridge (910) with end effector (1012). As can be seen in FIG. 21A, cartridge (910) and end effector (1012) are initially separated. In the position, platform (918) is in the flat configuration. In addition, power input (930) is not in communication with power output (1040), so platform (918) cannot be transitioned to the expanded configuration. Thus, when cartridge (910) and end effector (1012) are initially separated, power input (930) and power output (1040) functionally act as a functional lockout feature to prevent inadvertent or premature deployment of buttress assemblies (110, 112).

Next, as can be seen in FIG. 21B, cartridge (910) is moved into position within end effector (1012) by either moving end effector (1012) relative to cartridge (910) or cartridge relative to end effector (1012). In this position, open end (912) of cartridge (910) is inserted into end effector (1012) to permit engagement between power input (930) and power output (1040). Once power input (930) and power output (1040) are engaged, platform (918) can be expanded by rotating power input (930) via power output (1040) to deploy buttress assemblies (110, 112) onto anvil (1018) and staple cartridge (1037). Because engagement between power input (930) and power output (1040) is needed for expansion of platform (918), it should be understood that power input (930) and power output (1040) act as an alignment features to promote proper placement of buttress assemblies (110, 112).

In some uses, power output (1040) may be incorporated into the drive for firing beam (1014) and/or other operational components of end effector (1012). In such examples, it should be understood that power output (1040) may rotate in one direction to drive firing beam (1014) and/or other operational components of end effector (1012). Meanwhile, power output (1040) may rotate in an opposite direction to drive expansion of platform (918) via power input (930). In some examples, such an operational feature may be desirable to prevent inadvertent operation of end effector (1012) (e.g., firing of firing beam (1014)) prematurely such as during deployment of buttress assemblies (110, 112).

E. Exemplary Alternative Applicator Device with Locating Features

Figure 23:
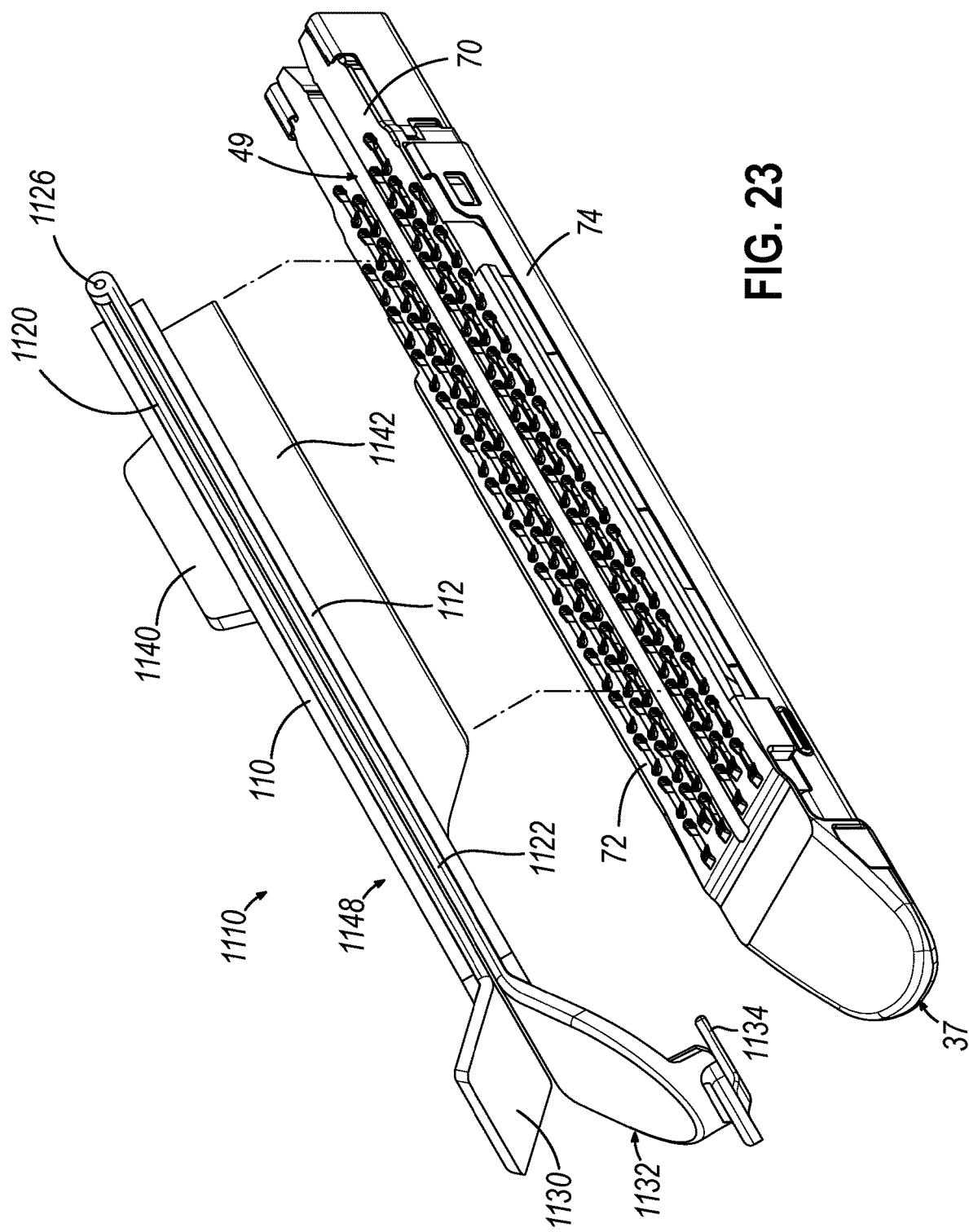
FIG. 23 depicts a perspective view of still another buttress applier cartridge that may be used to carry and apply the buttress assemblies of FIG. 8, showing the buttress applier cartridge being positioned onto a staple cartridge of the end effector of FIG. 3.

FIG. 23 shows another exemplary buttress applier cartridge (1110) (also referred to as a "buttress applicator") that may be used to support, protect, and apply adjunct material, such as buttress assemblies (110, 112), to an end effector. Buttress applier cartridge (1110) of the present example is substantially similar to buttress applier cartridge (510) described above except where otherwise explicitly described herein. For instance, as with cartridge (510), cartridge (1110) of this example comprises a platform (1118) configured to expand or otherwise move to apply buttress assemblies (110, 112) to an end effector. Although not shown, it should be understood that in other examples, cartridge (1110) may also include other additional features similar to housing.

As with platform (518) described above, platform (1118) of the present example is configured to support a pair of buttress assemblies (110) on one side of platform (1118) and another pair of buttress assemblies (112) on the other side of platform (1118). Also as with platform (518), platform (1118) of the present example is generally configured to be expandable to apply buttress assemblies (110, 112). To support such expandability, platform (1118) includes an upper support (1120), and a lower support (1122) connected with a hinge (1126). Upper support (1120) comprises an elongate flat surface configured for support of buttress assembly (110). Meanwhile, lower support (1122) also comprises an elongate flat surface configured for support of buttress assembly (112).

Upper support (1120) is connected to lower support (1122) at hinge (1126). Hinge (1126) is positioned at the proximal end of each support (1120, 1122) such that hinge (1126) is generally configured for insertion into an end effector (12), as will be described in greater detail below. Hinge (1126) is generally configured to permit pivoting of upper support (1120) relative to lower support (1122).

Unlike platform (518) described above, platform (1118) of the present example is configured to expand manually through actuation by an operator. To facilitate such manual expansion, platform (1118) of the present example further includes a manipulation tab (1130) and a lock tab (1132). Manipulation tab (1130) extends distally from upper support (1120) and is generally configured for gasping by an operator to manually pull or otherwise manipulate upper support (1120) about hinge (1126).

Lock tab (1132) extends distally from lower support (1122). As will be described in greater detail below, lock tab (1132) is generally configured to fasten to staple cartridge (37) of end effector (12) to secure lower support (1122) to staple cartridge (37). To facilitate such fastening, lock tab (1132) is generally shaped to correspond to the shape of the distal end of staple cartridge (37). In addition, lock tab (1132) includes a lock tooth (1134) extending proximally from a distal end of lock tab (1132). As will be understood, lock tooth (1134) is generally configured to engage a portion of staple cartridge (37) to releasably secure lock tab (1132) to staple cartridge (37).

Platform (1118) further includes an upper insert (1140) and a lower insert (1142) extending from upper support (1120) and lower support (1122), respectively. As will be described in greater detail below, both upper insert (1140) and lower insert (1142) are configured to engage portions of end effector (12)/staple cartridge (37) to provide a locating feature or mechanical ground to ensure proper positioning of cartridge (1110) within end effector (12). Lower support (1122) is additionally beneficial to detect certain features of end effector (12) (e.g., wedge sled (41)) to prevent use of cartridge (1110) with end effector (12) in an improper state (e.g., after firing of wedge sled (41)).

Upper insert (1140) extends upwardly from an upper surface of upper support (1120). The particular size and shape of upper insert (1140) is generally configured to permit receipt of upper insert (1140) into longitudinal anvil slot (42) of anvil (18). As will be understood, this configuration permits upper insert (1140) to ensure proper positioning of upper support (1120) relative to anvil (18) for proper application of buttress assembly (110). In other words, upper insert (1140) is configured to act similarly to a go-no-go gauge to prevent application of buttress assembly (110) when cartridge (1110) is mis-aligned or used with an improper end effector (12) entirely.

Lower insert (1142) extends downwardly from a lower surface of lower support (1122). The particular size and shape of lower insert (1142) is generally configured to permit receipt of lower insert (1142) into vertical slot (49) of staple cartridge (37). As will be understood, this configuration permits lower insert (1142) to ensure proper positioning of lower support (1122) relative to staple cartridge (37). In addition, lower insert (1142) is configured to prevent use of cartridge (1110) when staple cartridge (37) is in a fired state. As will be understood, this functionality is generally provided by lower insert (1142) being shaped to avoid wedge sled (41) when wedge sled (41) is in a home or unfired position. Meanwhile, lower insert (1142) is also shaped to contact wedge sled (41) when wedge sled (41) is in a fired position to thereby block full insertion of cartridge (1110) into end effector (12).

Figure 24A:
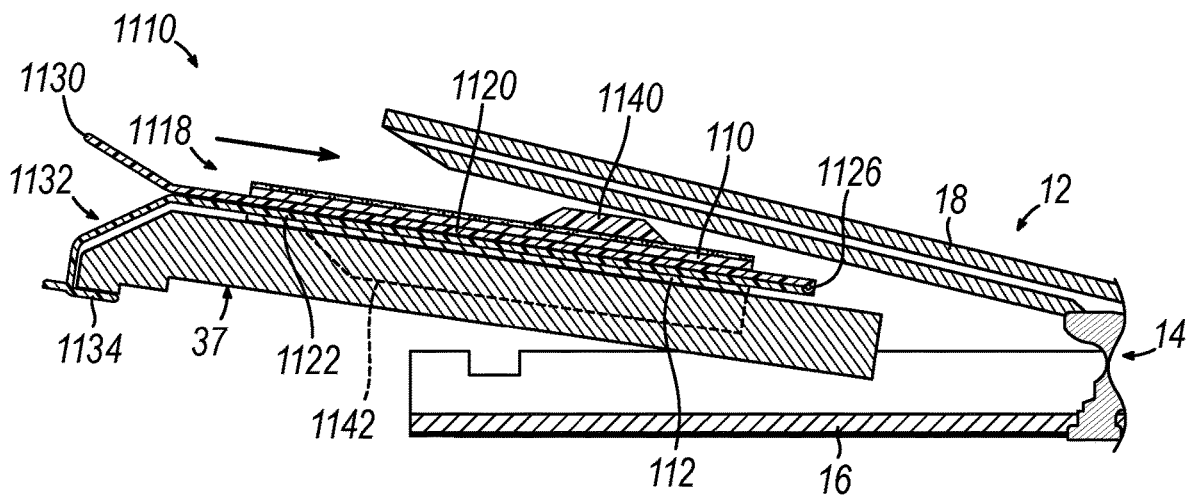
FIG. 24A depicts a side cross-sectional view of the buttress applier cartridge and staple cartridge of FIG. 23 and the end effector of FIG. 3, showing the buttress applier cartridge and staple cartridge being inserted into a lower jaw of the end effector.
Figure 24B:
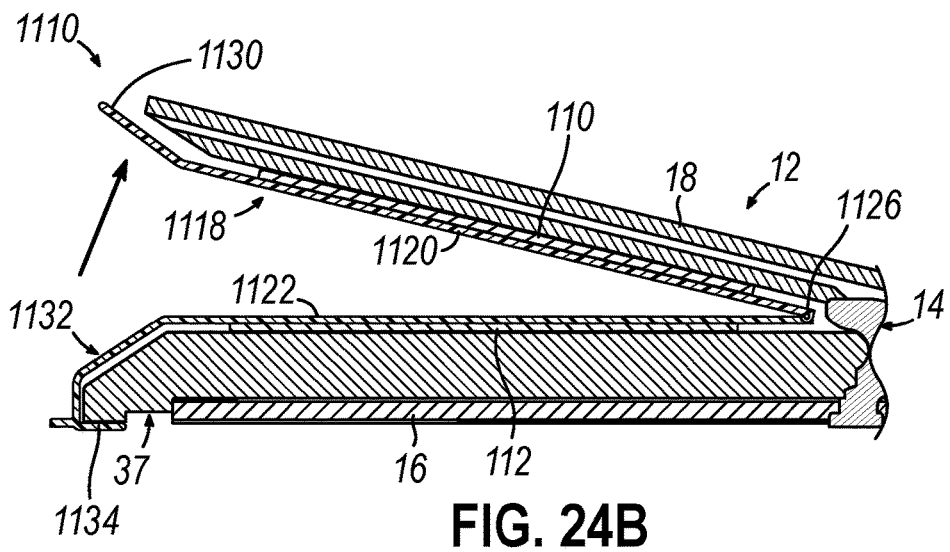
FIG. 24B depicts another side cross-sectional view of the buttress applier cartridge and staple cartridge of FIG. 23 and the end effector of FIG. 3, showing the buttress applier cartridge and staple cartridge being fully inserted into the lower jaw of the end effector and a platform of the buttress applier cartridge in an expanded configuration.
Figure 24C:
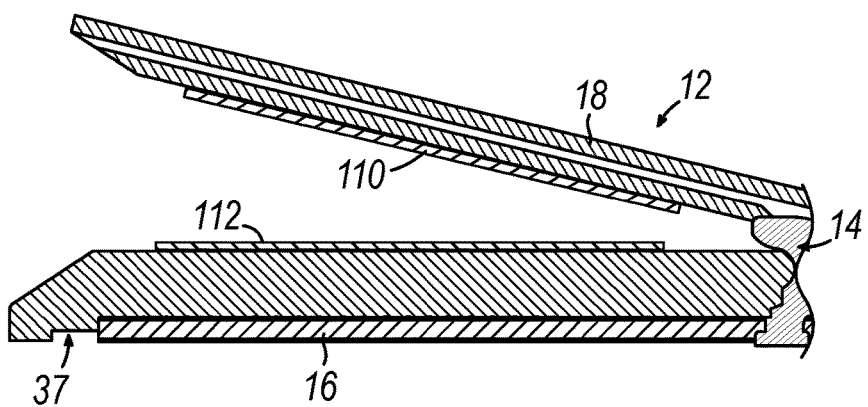
FIG. 24C depicts a side cross-sectional view of the end effector of FIG. 3 after the buttress applier cartridge of FIG. 23 has been removed from the end effector.

FIGS. 24A through 24C show an exemplary use of cartridge (1110) with end effector (12) to apply buttress assemblies (110, 112) to end effector (12)/staple cartridge (37). As can be seen in FIG. 24A, cartridge (1110) can initially be installed onto staple cartridge (37) prior to insertion of staple cartridge (37) into lower jaw (16) of end effector (12). Cartridge (1110) can be installed onto staple cartridge (37) by inserting lower inert (1142) into vertical slot (49) of staple cartridge (37) and then snapping lock tab (1132) onto the distal end of staple cartridge (37). Incidentally, the step of installing cartridge (1110) onto staple cartridge (37) may also include application of buttress assembly (112) to upper deck (72) of staple cartridge (37).

Although the present use shows cartridge (1110) being installed onto staple cartridge (37) prior to insertion of staple cartridge (37) into lower jaw (16) of end effector (12), it should be understood that in other uses, staple cartridge (37) may be readily inserted into lower jaw (16) first. In such an alternative use, cartridge (1110) may then be installed onto staple cartridge (37) once staple cartridge (37) is inserted into lower jaw (16).

Regardless of the particular order of installation of cartridge (1110) to staple cartridge (37) and staple cartridge (37) to lower jaw (16), once both components are installed, upper support (1120) of cartridge (1110) may be used to apply buttress assembly (110). In particular, and as best seen in FIG. 24B, buttress assembly (110) can be applied by an operator grasping manipulation tab (1130) and pivoting upper support (1120) about hinge (1126) upwardly towards anvil (18). Upper insert (1140) can then be received by longitudinal anvil slot (42) to ensure proper alignment between upper support (1120) and anvil (18). Upon receipt of upper insert (1140) into longitudinal anvil slot (42), upper support (1120) may be further pivoted about hinge (1126) to apply buttress assembly (110) to anvil (18).

After buttress assembly (110) is applied to anvil (18) as described above, cartridge (1110) can be removed from end effector (12) as shown in FIG. 24C. With cartridge (1110) removed, end effector (12) may then be used in a procedure.

F. Exemplary Alternative Applicator Device with Reuse Lock

Figure 25:
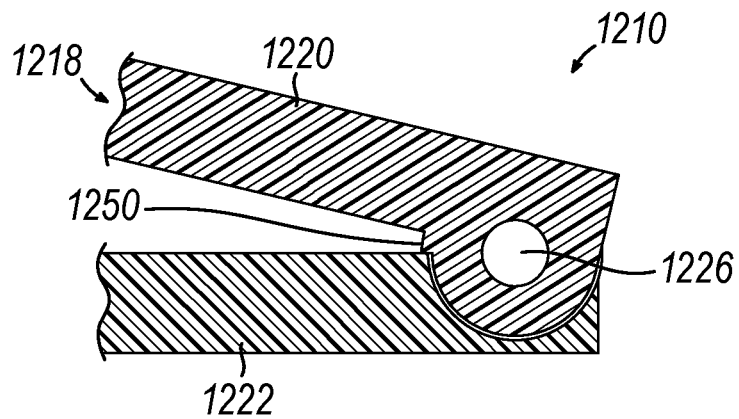
FIG. 25 depicts a partial side cross-sectional view of still another buttress applier cartridge that may be used to carry and apply the buttress assemblies of FIG. 8.

In some buttress applier cartridges similar to buttress applier cartridge (1110) described above, it may be desirable to include certain features to prevent or discourage reuse of the cartridge after application of buttress assemblies (110, 112). FIG. 25 shows an exemplary alternative buttress applier cartridge (1210) that is substantially similar to buttress applier cartridge (1110) described above unless otherwise explicitly described herein. For instance, like with cartridge (1110), cartridge (1210) of this example includes a platform (1218) having an upper support (1220) and a lower support (1222). Although not shown, it should be understood that upper support (1220) and lower support (1222) may include structures similar manipulation tab (1130), lock tab (1132), upper insert (1140) and lower insert (1142).

Cartridge (1210) also includes a hinge (1226) similar to hinge (1126) described above. However, unlike hinge (1126), hinge (1226) of the present example includes a one-way stop (1250). One-way stop (1250) is generally configured to act as a ratchet mechanism by permitting hinge (1226) to open, while preventing complete re-closure after opening. In the present example, one-way stop (1250) is configured as a protrusion or detent feature integrated into a portion of hinge (1226) to permit rotation of upper support (1220) in one direction, but prevent rotation of upper support (1220) in another direction after upper support (1220) has passed a certain predetermined point of rotation.

Although one-way stop (1250) is shown in the present example as being integrated into hinge (1226), it should be understood that in other examples, one-way stop (1250) can be readily integrated into other components of cartridge (1210). Alternatively, in other examples, one-way stop (1250) can be an entirely separate component attached to one or more elements of cartridge (1210). Various alternative configurations for one-way stop (1250) will be apparent to those of ordinary skill in the art in view of the teachings herein.

In use, cartridge (1210) can be used as similarly described above with respect to cartridge (1110). For instance, cartridge (1210) can be first installed onto staple cartridge (37). The combination of cartridge (1210) and staple cartridge (37) can then be inserted into lower jaw (16) of end effector (12). Upper support (1220) can then be pivoted about hinge relative to lower support (1222) to apply buttress assembly (110). However, unlike the use described above, it should be understood that once support (1220) is pivoted past a certain point, one-way stop (1250) functions to prevent pivoting in the reverse direction. Thus, upon removal of cartridge (1210) after application of buttress assemblies (110, 112), cartridge (1210) may remain in an at least partially open state to provide an affirmative indication of previous use and thereby discourage reuse thereof. Although one-way stop (1250) prevents some reverse pivoting of upper support (1220), it should be understood that at least some reverse pivoting may still be permitted to permit removal of cartridge (1210) from end effector (12) after application of buttress assemblies (110, 112).

G. Exemplary Alternative Applicator Device with Liner

Figure 26A:
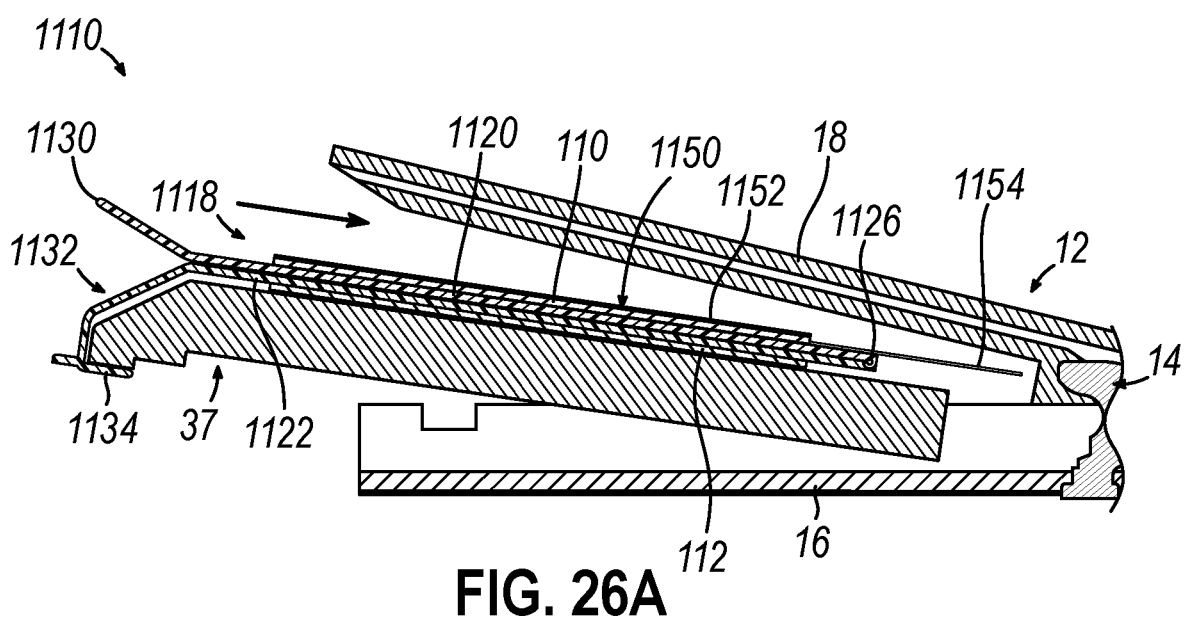
FIG. 26A depicts still another side cross-sectional view of the buttress applier cartridge and staple cartridge of FIG. 23, showing the buttress applier cartridge and staple cartridge being inserted into the end effector of FIG. 3 with a liner positioned on the buttress applier cartridge.

In examples, it may be desirable to use buttress assemblies (110, 112) described above with a single-use pre-applied liner. Such a liner may be desirable to protect buttress assemblies (110, 112) until application thereof onto an end effector. As can be seen in FIG. 26A shows buttress applier cartridge (1110) described above with an added liner (1150) disposed over buttress assembly (110). Although liner (1150) is described herein as being used with cartridge (1110), it should be understood that liner (1150) described below can be alternatively used with any other cartridge (210, 410, 510, 710, 810, 1210) described herein.

Liner (1150) of the present example is a single material covering that is configured to cover buttress assembly (110). In the present example, liner (1150) comprises a material of paper or polymer. In other examples, various alterative materials can be used. Additionally, in addition or in the alternative, such materials of liner (1150) can be coated with one or more coating layers of various materials such as wax, polymer, alloy, combinations of different materials, and/or etc.

Liner (1150) includes a cover portion (1152) and an excess portion (1144). Cover portion (1152) corresponds to the size and shape of buttress assembly (110) to cover buttress assembly (110). Meanwhile, excess portion (1144) extends proximally from buttress assembly (110). As will be described in greater detail below, excess portion (11044) is generally configured to engage a portion of end effector (12) to provide a visual cue for removal of liner (1150).

Figure 26B:
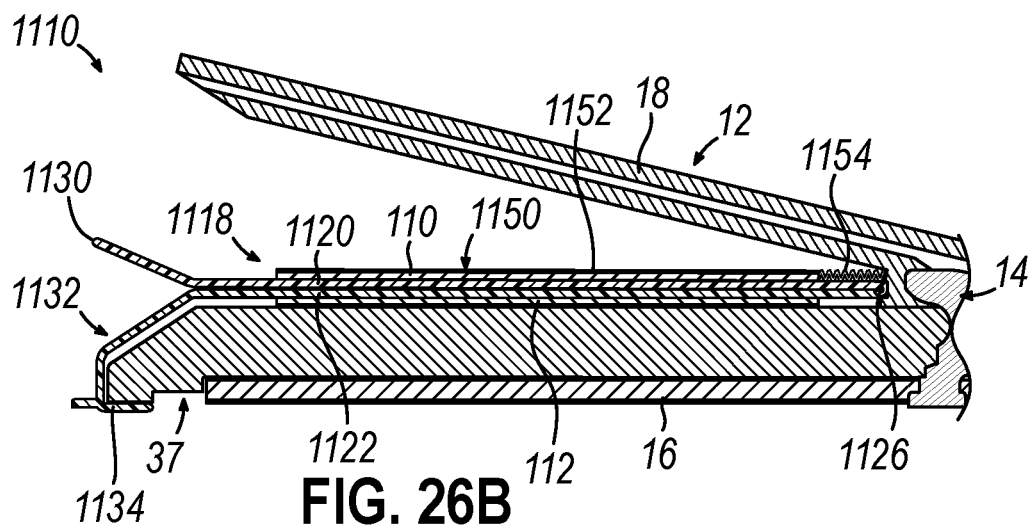
FIG. 26B depicts still another side cross-sectional view of the buttress applier cartridge and staple cartridge of FIG. 23, showing the buttress applier cartridge being fully inserted into the end effector of FIG. 3 and the liner of FIG. 26A engaged with the end effector.

FIGS. 26A and 26B show an exemplary use of cartridge (1110) with liner (1150). It should be understood that use of cartridge (1110) with liner (1150) is substantially similar to the use described above with respect to FIGS. 24A through 24C, unless otherwise explicitly described herein. For instance, as described above, cartridge (1110) may be first installed onto staple cartridge (37) and then both cartridge (1110) and staple cartridge (37) can be inserted into lower jaw (16) of end effector (12). However, unlike the use described above, in the use here, liner (1150) is pre-applied to cartridge (1110) such that liner (1150) is also inserted into lower jaw (16) along with cartridge (1110) and staple cartridge (37) as can be seen in FIG. 26A.

As cartridge (1110) is inserted into lower jaw (16), excess portion (1144) engages the crotch of end effector (12) formed at the intersection of lower jaw (16) and anvil (18). This engagement causes excess portion (1144) of liner (1150) to compact, roll, or bunch-up in the space between the crotch of end effector (12) and buttress assembly (110). This change of excess portion (1044) may provide an operator with a visual cue to remind the operator to remove liner (1150) prior to proceeding. Although not show, it should be understood that in some examples such functionality of excess portion (1144) can be added by excess portion (1144) including a T-shaped or otherwise expanded proximal end to avoid the possibility of excess portion (1144) remaining longitudinally extended by entering portions of end effector (12).

Liner (1150) can next be removed by an operator gasping excess portion (1144) or other portions of liner (1150) configured to aid removal (e.g., a removal tab). Once liner (1150) is removed, buttress assembly (110) can then be applied to anvil (18) by an operator gasping manipulation tab (1130) and pivoting upper support (1120) as similarly described above with respect to FIG. 24B. Cartridge (1110) can then be removed and end effector (12) can be readily used in a procedure.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: a platform including an upper support and a lower support; an adjunct material positioned on the upper support or the lower support, wherein the upper support is configured to move relative to the lower support in a direction toward a jaw of an end effector of a surgical stapler to apply the adjunct material to the jaw; and an engagement feature, wherein the engagement feature is configured to interact with a predetermined portion of the end effector to permit movement of the upper support relative to the lower support and thereby apply the adjunct material to the jaw of the end effector, wherein the engagement feature is configured to inhibit movement of the upper support relative to the lower support when the engagement feature is disengaged from the predetermined portion of the end effector.

Example 2

The apparatus of Example 1, wherein the engagement feature includes an actuator having an engagement portion, wherein the engagement portion is configured to engage the predetermined portion of the end effector to move the actuator and thereby permit movement of the upper support relative to the lower support.

Example 3

The apparatus of Example 2 further comprising a gripping feature, wherein the gripping feature is movable relative to the platform to drive movement of the upper support relative to the lower support.

Example 4

The apparatus of Example 3, wherein the actuator is configured to engage a portion of the gripping feature to stop movement of the gripping feature relative to the platform.

Example 5

The apparatus of Examples 3 or 4, wherein the actuator includes a release opening, wherein the actuator is configured to move the release opening relative to the gripping feature to selectively lock and unlock movement of the gripping feature.

Example 6

The apparatus of any one or more of Examples 1 through 6, wherein the engagement feature includes a probe having a keyed end, wherein the keyed end is configured to mate with the predetermined portion of the end effector, wherein the keyed end is configured to engage the corresponding portion of the end effector to permit movement of the upper support relative to the lower support.

Example 7

The apparatus of Example 6, further comprising a latch configured to couple the upper support to the lower support, wherein the keyed end is configured to translate in response to engagement with the corresponding portion of the end effector to thereby decouple the upper support from the lower support.

Example 8

The apparatus of Example 7, further comprising a spring, wherein the spring is configured to drive movement of the upper support relative to the lower support upon decoupling of the latch from the upper support.

Example 9

The apparatus of Example 7, further comprising a spring and a dashpot, wherein the spring is configured to drive movement of the upper support relative to the lower support upon decoupling of the latch from the upper support, wherein the dashpot is configured to dampen movement driven by the spring.

Example 10

The apparatus of any one or more of Examples 7 through 9, wherein the latch includes an elongate member configured to rotate relative to the lower support, wherein the actuator includes an elongate pusher configured to rotate the elongate member of the latch.

Example 11

The apparatus of any one or more of Examples 1 through 10, wherein the adjunct material includes a first buttress assembly and a second buttress assembly, the first buttress assembly positioned on the upper support and the second buttress assembly positioned on the lower support.

Example 12

The apparatus of any one or more of Examples 1 through 11, further comprising a motor, and a power source in communication with the motor, wherein the motor is in communication with at least the upper support to drive movement of the upper support relative to the lower support, wherein the engagement feature is configured to activate the motor in response to engagement with the predetermined portion of the end effector.

Example 13

The apparatus of any one or more of Examples 1 through 12, wherein the engagement feature includes an upper insert and a lower insert, wherein the upper insert extends upwardly from the upper support, wherein the lower insert extends downwardly from the lower support.

Example 14

The apparatus of Example 13, wherein the upper insert is configured to engage an anvil of the end effector, wherein the lower support is configured to engage a staple cartridge of the end effector.

Example 15

The apparatus of Example 14, wherein the upper support is configured to pivot relative to the lower support to drive engagement between the upper insert and the anvil of the end effector.

Example 16

An apparatus comprising: an end effector, the end effector including: an anvil, and a jaw configured to support a plurality of staples, wherein the anvil and the jaw are pivotable relative to one another to clamp tissue; a buttress applier cartridge, wherein the buttress applier cartridge includes: a platform having a lower support and an upper support, wherein the upper support is configured to more relative to the lower support to transition the platform to an expanded configuration, and an end effector engagement assembly configured to permit the transition of the platform to the expanded configuration when a portion of the end effector engagement assembly engages a portion of the end effector; and a buttress assembly positioned on the upper support or the lower support of the buttress applier cartridge such that the upper support or the lower support is configured to apply the buttress assembly to the end effector when the platform is in the expanded configuration.

Example 17

The apparatus of Example 16, wherein the end effector engagement assembly includes a probe, the probe having an engagement portion keyed to a portion of the end effector, wherein the engagement portion is configured to engage the end effector when the buttress applier cartridge is aligned with the anvil and the lower jaw of the end effector.

Example 18

The apparatus of Example 16 or 17, wherein the end effector engagement assembly includes a first locator and a second locator, wherein the first locator is configured for receipt within at least a portion of the anvil, wherein the second locator is configured for rescript within at least a portion of the jaw.

Example 19

A method comprising: inserting a lower insert of a buttress applier cartridge into a slot of an unspent staple cartridge to apply a first buttress assembly onto an upper deck of the staple cartridge from a lower support platform of the buttress applier cartridge; moving an upper support platform of the buttress applier cartridge relative to the lower support platform to insert an upper insert of the buttress applier cartridge into an anvil slot of an anvil of a surgical stapler end effector; and applying a second buttress assembly onto the anvil using the movement of the upper support platform while the upper insert is received within the anvil slot.

Example 20

The method of Example 19, further comprising the step of inserting the unspent staple cartridge into a lower jaw of the surgical stapler end effector after the step of inserting the lower insert into the slot of the unspent staple cartridge.

Example 21

The apparatus of any one or more of Examples 1 through 18, further comprising a linkage assembly in communication with the upper support and lower support of the platform, wherein a portion of the linkage assembly is configured to rotate or translate to drive the upper support and lower support away from each other.

Example 22

The apparatus of any one or more of Examples 1 through 18 and 21, wherein at least a portion of the platform is configured to removably couple to the end effector.

Example 23

The apparatus of any one or more of Examples 1 through 18 and 21 through 22, further comprising a housing having an open end and a closed end, wherein the open end of the housing is configured to receive a distal end of the end effector.

Example 24

The method of Example 19, further comprising the step of engaging an end effector engagement assembly of the buttress applier cartridge with a predetermined portion of the surgical stapler end effector, wherein the step of engaging the end effector engagement assembly with the predetermined portion of the surgical stapler end effector permits movement of the upper support platform relative to the lower support platform.

Example 25

The method of Example 24, wherein the predetermined portion of the surgical stapler end effector is a cutting edge.

Example 26

The method of Example 24, wherein the predetermined portion of the surgical stapler end effector is a lockout feature.

Example 27

The method of any one or more of Examples 19 and 24 through 26, wherein the step of moving the upper support platform relative to the lower support platform includes releasing a spring-loaded driving assembly in communication with the upper support platform and the lower support platform.

Example 28

The method of any one or more of Examples 19 and 24 through 26, wherein the step of moving the upper support platform relative to the lower support platform includes driving a linkage assembly in communication with the upper support platform and the lower support platform.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. Ser. No. 17/022,186, entitled "Apparatus and Method to Apply Buttress to End Effector of Surgical Stapler via Fixed Base," filed on Sep. 16, 2020; U.S. Pat. App. Ser. No. 17/022,209, entitled "Apparatus and Method to Apply Buttress to End Effector of Surgical Stapler via Driven Member," filed on Sep. 16, 2020; U.S. Pat. App. Ser. No. 17/022,214, entitled "Apparatus and Method to Apply Buttresses Separately to Jaws of End Effector of Surgical Stapler," filed on Sep. 16, 2020; U.S. Pat. App. Ser. No. 17/022,414, entitled "Apparatus and Method to Close End Effector of Surgical Stapler onto Buttress," filed on Sep. 16, 2020; U.S. Pat. App. Ser. No. 17/022,419, entitled "Apparatus and Method to Detect Full Seating of Buttress Applicator in End Effector of Surgical Stapler," filed on Sep. 16, 2020; and/or U.S. Pat. App. Ser. No. 17/022,520, entitled "Method of Applying Buttress to End Effector of Surgical Stapler," filed on Sep. 16, 2020. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a platform including an upper support and a lower support;
   (b) an adjunct material positioned on the upper support or the lower support, wherein the upper support is configured to move relative to the lower support in a direction toward a jaw of an end effector of a surgical stapler to apply the adjunct material to the jaw; and
   (c) an engagement feature, wherein the engagement feature is configured to interact with a predetermined portion of the end effector to permit movement of the upper support relative to the lower support and thereby apply the adjunct material to the jaw of the end effector, wherein the engagement feature is configured to inhibit movement of the upper support relative to the lower support when the engagement feature is disengaged from the predetermined portion of the end effector.

2. The apparatus of claim 1, wherein the engagement feature includes an actuator having an engagement portion, wherein the engagement portion is configured to engage the predetermined portion of the end effector to move the actuator and thereby permit movement of the upper support relative to the lower support.

3. The apparatus of claim 2, further comprising a gripping feature, wherein the gripping feature is movable relative to the platform to drive movement of the upper support relative to the lower support.

4. The apparatus of claim 3, wherein the actuator is configured to engage a portion of the gripping feature to stop movement of the gripping feature relative to the platform.

5. The apparatus of claim 4, wherein the actuator includes a release opening, wherein the actuator is configured to move the release opening relative to the gripping feature to selectively lock and unlock movement of the gripping feature.

6. The apparatus of claim 1, wherein the engagement feature includes a probe having a keyed end, wherein the keyed end is configured to mate with the predetermined portion of the end effector, wherein the keyed end is configured to engage the corresponding portion of the end effector to permit movement of the upper support relative to the lower support.

7. The apparatus of claim 6, further comprising a latch configured to couple the upper support to the lower support, wherein the keyed end is configured to translate in response to engagement with the corresponding portion of the end effector to thereby decouple the upper support from the lower support.

8. The apparatus of claim 7, further comprising a spring, wherein the spring is configured to drive movement of the upper support relative to the lower support upon decoupling of the latch from the upper support.

9. The apparatus of claim 7, further comprising a spring and a dashpot, wherein the spring is configured to drive movement of the upper support relative to the lower support upon decoupling of the latch from the upper support, wherein the dashpot is configured to dampen movement driven by the spring.

10. The apparatus of claim 9, wherein the latch includes an elongate member configured to rotate relative to the lower support, wherein the actuator includes an elongate pusher configured to rotate the elongate member of the latch.

11. The apparatus of claim 1, wherein the adjunct material includes a first buttress assembly and a second buttress assembly, the first buttress assembly positioned on the upper support and the second buttress assembly positioned on the lower support.

12. The apparatus of claim 1, further comprising a motor, and a power source in communication with the motor, wherein the motor is in communication with at least the upper support to drive movement of the upper support relative to the lower support, wherein the engagement feature is configured to activate the motor in response to engagement with the predetermined portion of the end effector.

13. The apparatus of claim 1, wherein the engagement feature includes an upper insert and a lower insert, wherein the upper insert extends upwardly from the upper support, wherein the lower insert extends downwardly from the lower support.

14. The apparatus of claim 13, wherein the upper insert is configured to engage an anvil of the end effector, wherein the lower support is configured to engage a staple cartridge of the end effector.

15. The apparatus of claim 14, wherein the upper support is configured to pivot relative to the lower support to drive engagement between the upper insert and the anvil of the end effector.

16. An apparatus comprising:
    (a) an end effector, the end effector including:
       (i) an anvil, and
       (ii) a jaw configured to support a plurality of staples, wherein the anvil and the jaw are pivotable relative to one another to clamp tissue;
    (b) a buttress applier cartridge, wherein the buttress applier cartridge includes:
       (i) a platform having a lower support and an upper support, wherein the upper support is configured to move relative to the lower support to transition the platform to an expanded configuration from a non-expanded configuration, and
       (ii) an end effector engagement assembly configured to permit the transition of the platform to the expanded configuration when a portion of the end effector engagement assembly engages a portion of the end effector; and
    (c) a buttress assembly positioned on the upper support or the lower support of the buttress applier cartridge such that the upper support or the lower support is configured to apply the buttress assembly to the end effector when the platform is in the expanded configuration.

17. The apparatus of claim 16, wherein the end effector engagement assembly includes a probe, the probe having an engagement portion keyed to a portion of the end effector, wherein the engagement portion is configured to engage the end effector when the buttress applier cartridge is aligned with the anvil and the lower jaw of the end effector.

18. The apparatus of claim 16, wherein the end effector engagement assembly includes a first locator and a second locator, wherein the first locator is configured for receipt within at least a portion of the anvil, wherein the second locator is configured for receipt within at least a portion of the jaw.

19. A method comprising:
(a) inserting a lower insert of a buttress applier cartridge into a slot of an unspent staple cartridge to apply a first buttress assembly onto an upper deck of the staple cartridge from a lower support platform of the buttress applier cartridge;
(b) moving an upper support platform of the buttress applier cartridge relative to the lower support platform to insert an upper insert of the buttress applier cartridge into an anvil slot of an anvil of a surgical stapler end effector; and
(c) applying a second buttress assembly onto the anvil using the movement of the upper support platform while the upper insert is received within the anvil slot.

20. The method of claim 19, further comprising the step of inserting the unspent staple cartridge into a lower jaw of the surgical stapler end effector after the step of inserting the lower insert into the slot of the unspent staple cartridge.

* * * * *